United States Patent
Ford et al.

(10) Patent No.: US 8,974,513 B2
(45) Date of Patent: *Mar. 10, 2015

(54) MEDICAL IMPLANT DETACHMENT SYSTEMS AND METHODS

(75) Inventors: Russell Ford, Palo Alto, CA (US); Scott McGill, San Ramon, CA (US); Clifford Teoh, Los Altos, CA (US); Michael Williams, Oakland, CA (US); Kamal Ramzipoor, Fremont, CA (US); Like Que, Livermore, CA (US); Ann Huang, Fremont, CA (US); Elena Oo, Fremont, CA (US); Christina Ma, Fremont, CA (US); Stella Chu, Fremont, CA (US)

(73) Assignees: Stryker Corporation, Kalamazoo, MI (US); Stryker NV Operations Limited, Dublin (IE)

( * ) Notice: Subject to any disclaimer, the term of this patent is extended or adjusted under 35 U.S.C. 154(b) by 26 days.

This patent is subject to a terminal disclaimer.

(21) Appl. No.: 13/540,514

(22) Filed: Jul. 2, 2012

(65) Prior Publication Data

US 2012/0271344 A1 Oct. 25, 2012

Related U.S. Application Data

(63) Continuation of application No. 12/122,636, filed on May 16, 2008, now Pat. No. 8,221,483.

(60) Provisional application No. 60/939,032, filed on May 18, 2007.

(51) Int. Cl.
*A61F 2/06* (2013.01)
*A61B 17/12* (2006.01)
*A61B 17/00* (2006.01)

(52) U.S. Cl.
CPC ..... *A61B 17/12022* (2013.01); *A61B 17/12145* (2013.01); *A61B 2017/12063* (2013.01); *A61B 2017/00022* (2013.01); *A61B 17/12154* (2013.01); *A61B 17/12113* (2013.01)
USPC ........................... 623/1.11; 606/200; 606/198

(58) Field of Classification Search
CPC .................. A61F 17/12022; A61F 17/12109; A61F 17/12131; A61F 17/1214
USPC ......... 606/191, 194, 198, 108, 200; 623/1.11; 439/909, 578
See application file for complete search history.

(56) References Cited

U.S. PATENT DOCUMENTS

| | | | |
|---|---|---|---|
| 4,994,069 A | 2/1991 | Ritchart et al. | |
| 5,122,136 A | 6/1992 | Guglielmi et al. | |

(Continued)

FOREIGN PATENT DOCUMENTS

| | | |
|---|---|---|
| DE | 10325130 | 9/2004 |
| EP | 2444010 A2 | 4/2012 |

(Continued)

OTHER PUBLICATIONS

Boston Scientific Scimed, Inc., International Search Report and Written Opinion mailed Dec. 13, 2010, in corresponding International Application No. PCT/US20101026831, filed Mar. 10, 2010.

(Continued)

*Primary Examiner* — Katrina Stransky
(74) *Attorney, Agent, or Firm* — Vista IP Law Group LLP

(57) ABSTRACT

An implant assembly comprises an elongated pusher member, and an implantable device (e.g., a vaso-occlusive device) mounted to the distal end of the pusher member. The implant assembly further comprises an electrolytically severable joint disposed on the pusher member, wherein the implantable device detaches from the pusher member when the severable joint is severed, and a return electrode carried by the distal end of the pusher member (e.g., a coil disposed about the pusher member) in proximity to, but electrically isolated from, the severable joint. The implant assembly further comprises a terminal carried by the proximal end of the pusher member in electrical communication with the severable joint.

9 Claims, 6 Drawing Sheets

(56) References Cited

U.S. PATENT DOCUMENTS

| | | | |
|---|---|---|---|
| 5,226,911 | A | 7/1993 | Chee et al. |
| 5,304,194 | A | 4/1994 | Chee et al. |
| 5,382,259 | A | 1/1995 | Phelps et al. |
| 5,549,624 | A | 8/1996 | Mirigian et al. |
| 5,582,619 | A | 12/1996 | Ken |
| 5,690,666 | A | 11/1997 | Berenstein et al. |
| 5,919,187 | A | 7/1999 | Guglielmi et al. |
| 5,984,929 | A | 11/1999 | Bashiri et al. |
| 6,059,779 | A * | 5/2000 | Mills ................ 606/41 |
| 6,077,260 | A | 6/2000 | Wheelock et al. |
| 6,280,457 | B1 | 8/2001 | Wallace et al. |
| 6,409,721 | B1 | 6/2002 | Wheelock et al. |
| 6,468,266 | B1 | 10/2002 | Bashiri et al. |
| 6,589,230 | B2 | 7/2003 | Gia et al. |
| 6,953,473 | B2 | 10/2005 | Porter |
| 7,198,613 | B2 | 4/2007 | Gandhi et al. |
| 2002/0091380 | A1* | 7/2002 | Wheelock et al. ........ 606/32 |
| 2002/0151883 | A1 | 10/2002 | Guglielmi |
| 2004/0002732 | A1 | 1/2004 | Teoh et al. |
| 2004/0002733 | A1 | 1/2004 | Teoh |
| 2004/0010243 | A1 | 1/2004 | Klint |
| 2006/0135986 | A1 | 6/2006 | Wallace et al. |
| 2006/0271097 | A1 | 11/2006 | Ramzipoor et al. |
| 2006/0282112 | A1 | 12/2006 | Griffin |
| 2007/0055302 | A1 | 3/2007 | Henry |

FOREIGN PATENT DOCUMENTS

| | | |
|---|---|---|
| WO | 9942038 | 8/1999 |
| WO | 03053281 | 7/2003 |
| WO | 2008064206 | 5/2008 |
| WO | 2008085606 | 7/2008 |
| WO | 2008144587 | 11/2008 |

OTHER PUBLICATIONS

Boston Scientific Scimed, Inc., International Search Report and Written Opinion mailed Nov. 30, 2009, in corresponding International Application No. PCT/US20091059797, filed Oct. 7, 2009.

Boston Scientific Scimed, Inc., Invitation to Pay Additional Fees mailed Jan. 29, 2009, in corresponding International Application No. PCT/US2008/064013, filed May 16, 2008.

Boston Scientific Scimed, Inc., International Search Report and Written Opinion mailed May 16, 2009, in corresponding International Application No. PCT/US2008/064013, filed May 16, 2008.

Boston Scientific Scimed, Inc., International Search Report and Written Opinion mailed May 21, 2010, in corresponding International Application No. PCT/US2010/029700, filed Apr. 1, 2010.

Boston Scientific Scimed, Inc., Invitation to Pay Additional Fees mailed Jul. 23, 2010, in corresponding International Application No. PCT/US2010/026831, filed Mar. 10, 2010.

Boston Scientific Scimed, Inc., Article 94(3) Communication mailed Jul. 15, 2011 in corresponding European Application No. 08755795.5, filed May 16, 2008.

Japanese Laid Open Patent Publication No. H08-322941, in Japanese language, published Dec. 10, 1996, Applicant Target Therapeutics Inc., English Patent Abstract only, 13 pages.

Notice of Rejection for Japanese Patent Application No. 2010-509485, mailed Jan. 8, 2013, in Japanese language with English translation provided by Japanese associates, 8 pages.

EPO Communication including the extended European search report for EP Application No. 12000196.1, Applicant Stryker NV Operations Limited, et al., mailed Sep. 6, 2013, 9 pages.

EPO Communication pursuant to Article 94(3) EPC for EP Application No. 08755795.5. Applicant Boston Scientific Scimed, Inc., mailed Jul. 15, 2011, 5 pages.

* cited by examiner

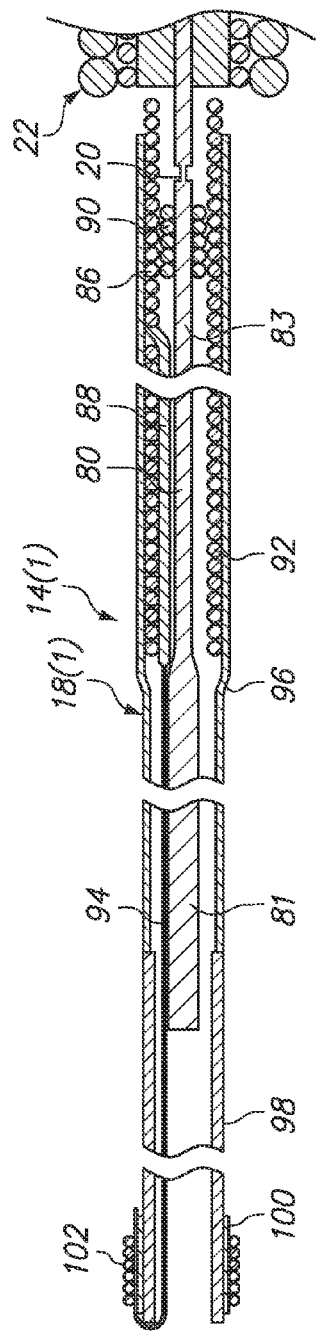
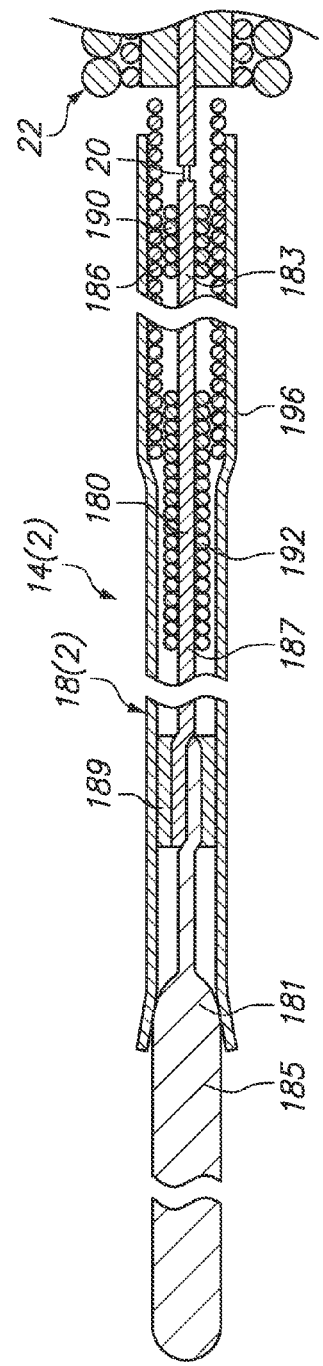
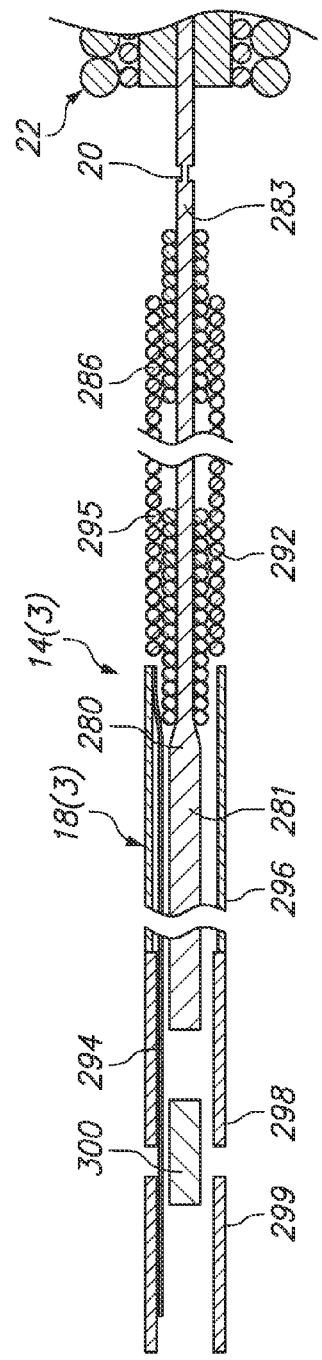
FIG. 5
FIG. 6
FIG. 7

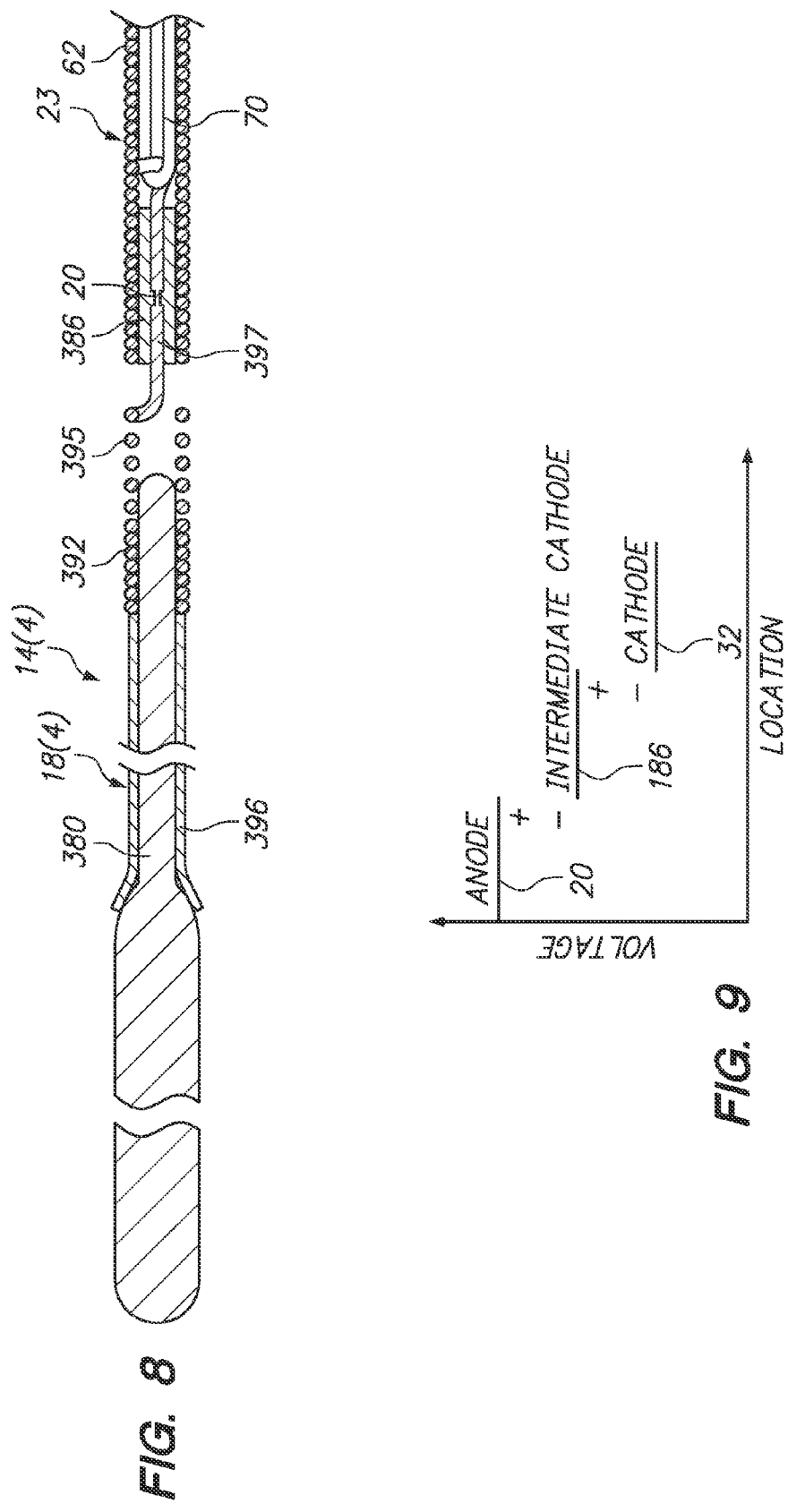

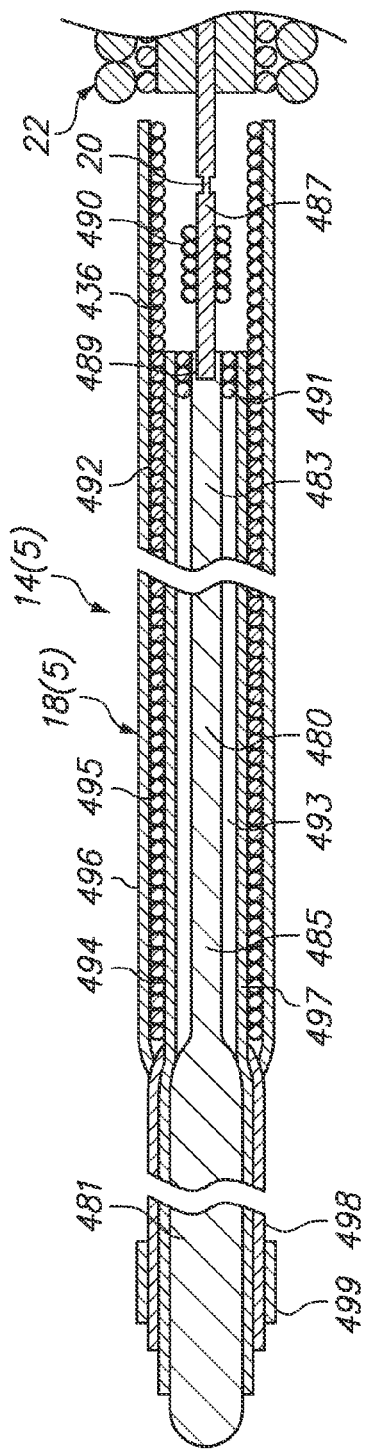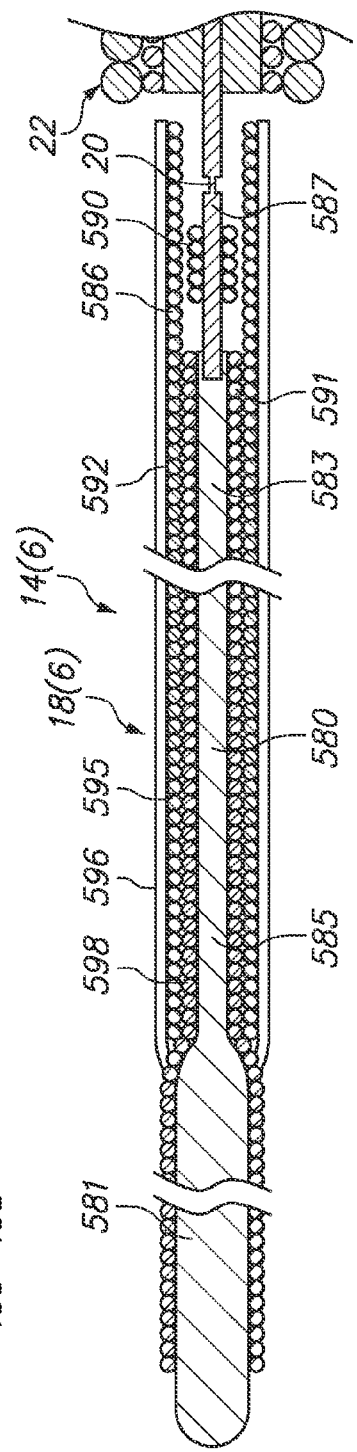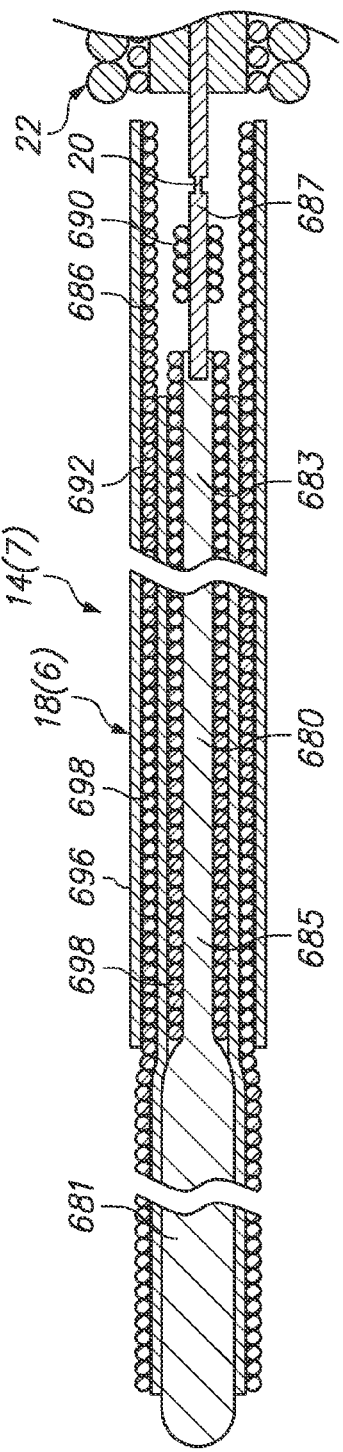

MEDICAL IMPLANT DETACHMENT SYSTEMS AND METHODS

CROSS-REFERENCE TO RELATED APPLICATIONS

The present application is a continuation of pending U.S. patent application Ser. No. 12/122,636, filed May 16, 2008, which claims the benefit under 35 U.S.C. §119 of U.S. Provisional Patent Application Ser. No. 60/939,032, filed May 18, 2007. The foregoing applications are each hereby incorporated by reference into the present application in their entirety.

FIELD OF THE INVENTION

The invention relates generally to implantable devices (e.g., embolic coils, stents, and filters) having flexible electrolytic detachment mechanisms.

BACKGROUND

Implants may be placed in the human body for a wide variety of reasons. For example, stents are placed in a number of different anatomical lumens within the body. They may be placed in blood vessels to cover vascular lesions or to provide patency to the vessels. Stents are also placed in biliary ducts to prevent them from kinking or collapsing. Grafts may be used with stents to promote growth of endothelial tissue within those vessels. As another example, vena cava filters can be implanted in the vena cava to catch thrombus sloughed off from other sites within the body and carried to the implantation site via the blood stream.

As still another example, vaso-occlusive devices are used for a wide variety of reasons, including for the treatment of intravascular aneurysms. An aneurysm is a dilation of a blood vessel that poses a risk to health from the potential for rupture, clotting, or dissecting. Rupture of an aneurysm in the brain causes stroke, and rupture of an aneurysm in the abdomen causes shock. Cerebral aneurysms are usually detected in patients as the result of a seizure or hemorrhage and can result in significant morbidity or mortality. Vaso-occlusive devices can be placed within the vasculature of the human body, typically via a catheter, either to block the flow of blood through a vessel making up that portion of the vasculature through the formation of an embolus or to form such an embolus within an aneurysm stemming from the vessel. The embolus seals and fills the aneurysm, thereby preventing the weakened wall of the aneurysm from being exposed to the pulsing blood pressure of the open vascular lumen.

One widely used vaso-occlusive device is a helical wire coil having windings, which may be dimensioned to engage the walls of the vessels. These coils typically take the form of soft and flexible coils having diameters in the range of 10-30 mils. Multiple coils will typically be deployed within a single aneurysm. There are a variety of ways of discharging vaso-occlusive coils into the human vasculature. In addition to a variety of manners of mechanically deploying vaso-occlusive coils into the vasculature of a patient, U.S. Pat. No. 5,122,136, issued to Guglielmi et al., describes an electrolytically detachable vaso-occlusive coil that can be introduced through a microcatheter and deployed at a selected location in the vasculature of a patient.

This vaso-occlusive coil is attached (e.g., via welding) to the distal end of an electrically conductive pusher wire. With the exception of a sacrificial joint just proximal to the attached embolic device, the outer surface of the pusher wire is coated with an ionically non-conductive material. Thus, the sacrificial joint will be exposed to bodily fluids when deployed within the patient. A power supply is used to provide power to the core wire, with a conductive patch or intravenous needle located on or in the patient providing a ground return path. Applying a positive voltage to the pusher wire via the power supply relative to the ground return causes an electrochemical reaction between the sacrificial joint and the surrounding bodily fluid (e.g., blood). As a result, the sacrificial joint will dissolve, thereby detaching the vaso-occlusive coil from the pusher wire at the selected site.

While the use of electrolytically detachable vaso-occlusive coils has generally been successful, the period of time needed to detach the vaso-occlusive coils from the pusher wire is relatively long (currently, averaging from 30 to 40 seconds) and variable, resulting in an increase in procedure time. This problem is compounded by the need to deploy multiple vaso-occlusive coils within the patient. The relatively long and varying detachment time is due, in large part, to the relatively large and widely varying tissue impedance between the sacrificial joint and the ground electrode amongst patients. In addition, the bodily fluid surrounding the sacrificial joint may not be the optimum electrolyte (compared with saline) for inducing an electrochemical reaction in the detachment zone, thereby increasing the detachment time. Blood environment may also introduce variability in detachment time due to the possibility of blood clotting and the variations in blood constituents amongst patients.

Theoretically, the voltage of the electrical energy supplied to the sacrificial joint can be increased in order to reduce the detachment time. However, an increased voltage may cause bubbling resulting from gas generation byproducts during the electrochemical reaction, which may insulate the detachment zone adjacent the sacrificial joint from the electrolyte, thereby slowing or stopping the electrochemical reaction, and at the least, causing variability in detachment time. In addition, because gas bubbles are more likely to be contained within the sheath of the microcatheter used to deliver the vaso-occlusive coil, delivery systems are often designed, such that the sacrificial joint extends a certain distance (e.g., 1 mm) from the distal tip of the microcatheter to accommodate dimensional tolerance stackup in the pusher wire and the microcatheter.

Exiting the microcatheter this far, however, degrades kickback performance (i.e., reaction of the microcatheter in response to detachment of the vaso-occlusive coil is to be minimized) due to the stiffness of the distal end of the pusher wire relative to the stiffness of the vaso-occlusive coil. In addition, locating the sacrificial joint this far from the distal tip of the microcatheter may cause it to come into contact with previously deployed vaso-occlusive coils, thereby shorting the sacrificial joint through the coils, resulting in an increase and/or variation in the detachment time. Notwithstanding the bubbling issue, it may sometimes be difficult to ascertain that the sacrificial joint is in contact with the blood, which must occur to initiate the electrochemical reaction and subsequent detachment of the vaso-occlusive coil.

SUMMARY OF THE INVENTION

In accordance with a one aspect of the present inventions, an implant assembly comprises an elongated pusher member, and an implantable device (e.g., a vaso-occlusive device) mounted to the distal end of the pusher member. The implant assembly further comprises an electrolytically severable joint disposed on the pusher member, wherein the implantable device detaches from the pusher member when the severable joint is severed. The implant assembly further comprises a return electrode carried by the distal end of the pusher member in proximity to, but electrically isolated from, the severable joint. For example, the return electrode may take the form of a coil disposed about the pusher member. The return electrode may be carried by the pusher member in such a manner that it remains with the implantable device or remains the pusher member when the severable joint is severed. The implant assembly further comprises a terminal carried by the proximal end of the pusher member in electrical communication with the severable joint. The use of a return electrode on the pusher member decreases the effective distance between the anodic severable joint and cathodic return electrode, thereby decreasing the detachment time and increasing the reliability, repeatability, and uniformity of the detachment process.

In one embodiment, the implant assembly further comprises another terminal carried by the proximal end of the pusher member in electrical communication with the return electrode. In another embodiment, the terminal in electrical communication with the severable joint is the only terminal carried by the proximal end of the pusher member. In an optional embodiment, one or both of the severable joint and return electrode comprise silver chloride in order to facilitate an electrolytic reaction between the severable joint and return electrode. For example, the severable joint and/or return electrode may comprise a silver core and a silver chloride coating. In another embodiment, the pusher member comprises an electrically conductive stiffening member through which the terminal and the severable joint are in electrical communication.

In accordance with another aspect of the present inventions, a medical system comprises an implant assembly that includes an elongated pusher member, an implantable device mounted to the distal end of the pusher member, an electrolytically severable joint disposed on the pusher member, wherein the implantable device detaches from the pusher member when the severable joint is severed, and a return electrode carried by the distal end of the pusher member in proximity to, but electrically isolated from, the severable joint. The detailed features of the implant assembly can be similar to those described above. The medical system further comprises an electrical power supply having a terminal electrically coupled to the severable joint; for example, via a terminal carried by the proximal end of the pusher member and/or an electrically conductive stiffening member of the pusher member.

In some embodiments, the power supply has another terminal electrically coupled to the return electrode (e.g., via another terminal carried by the proximal end of the pusher member) or electrically coupled to a ground electrode that is separate from the return electrode. In one embodiment, the power supply is configured for delivering direct current to the implant assembly. In another embodiment, the medical system further comprises a delivery catheter configured for slidably receiving the implant assembly.

In accordance with other aspect of the present inventions, a method of implanting a medical device (e.g., a vaso-occlusive device) within a patient is provided. The method comprises introducing the medical device within the patient via a pusher member (e.g., through a delivery catheter), conveying electrical energy (e.g., direct electrical current) to a joint disposed on the pusher member, and conveying electrical energy from a return electrode carried by the pusher member (e.g., a coil disposed about the pusher member) to induce an electrolytic reaction between the joint and the return electrode. As a result of the electrolytic reaction, the joint is severed to detach the medical device from the pusher member at a target site (e.g., an aneurismal sac) within the patient. The return electrode may, e.g., remain with the medical device when the joint is severed or remain with the pusher member when the joint is severed.

In one method, the electrolytic reaction comprises releasing chloride ions from the return electrode. The electrical energy may be conveyed to the joint via the pusher member, and the electrical energy may be conveyed from the return electrode via the pusher member or from the return electrode to a ground electrode via the tissue of the patient. In another method, the pusher member is removed from the patient.

In accordance with another aspect of the present inventions, an implant assembly comprises an elongated pusher member that has a stiffening member and an electrically conductive sheath (e.g., a coil, mesh, or braid) disposed over the stiffening member. The stiffening member may be composed of a suitable material, such as stainless steel, and the electrically conductive sheath may be composed of a suitable material, such as copper or silver. The implant assembly further comprises an implantable device (e.g., a vaso-occlusive device) mounted to the distal end of the pusher member. The implant assembly further comprises an electrolytically severable joint disposed on the pusher member, wherein the implantable device detaches from the pusher member when the severable joint is severed. The implant assembly further comprises a return electrode carried (e.g., mounted) by the distal end of the pusher member in proximity to, but electrically isolated from, the severable joint. In one embodiment, the return electrode takes the form of a coil disposed about the pusher member. The return electrode may be carried by the pusher member in such a manner that it remains with the implantable device or remains the pusher member when the severable joint is severed.

The implant assembly further comprises a terminal carried by the proximal end of the pusher member in electrical communication with the severable joint. The implant assembly further comprises an electrically conductive path extending between the terminal and one of the severable joint and the return electrode, wherein the electrically conductive path includes the electrically conductive sheath. The use of the electrically conductive sheath increases the conductance of the electrically conductive path between the terminal and the severable joint or return electrode, as compared to the case where a standard electrical conductor or the stiffening member is used without the electrically conductive sheath.

In one embodiment, the electrically conductive path extends between the terminal and the return electrode, in which case, the electrically conductive sheath and stiffening member are electrically isolated from each other. For example, the stiffening member may comprise an electrically conductive core wire and an electrically insulative coating disposed over the core wire, wherein the electrically insulative sheath is disposed over the electrically insulative coating. In another embodiment, the stiffening member has a proximal section having a first diameter and a distal section having a second decreased diameter, in which case, the electrically conductive path only extends between the terminal and the severable joint along the distal section of the stiffening member.

In another embodiment, the implant assembly further comprises another terminal carried by the proximal end of the pusher member in electrical communication with the return electrode, and the pusher member includes another electrically conductive sheath disposed over the stiffening member. In this case, the implant assembly may further comprise another electrically conductive path extending between the other terminal and another of the severable joint and the return electrode, such that the other electrically conductive path includes the other electrically conductive sheath.

In accordance with a further aspect of the present inventions, another implant assembly is provided. The implant assembly comprises an elongated pusher member, an implantable device mounted to the distal end of the pusher member, an electrolytically severable joint disposed on the pusher member, a terminal carried by the proximal end of the pusher member, and the implant assembly further comprises an electrically conductive path extending between the terminal and the severable joint, wherein the electrically conductive path includes the electrically conductive sheath. The features of the implant assembly can be the same as those described above.

In accordance with still another aspect of the present inventions, a medical system comprises either of the implant assemblies described above, and an electrical power supply having a terminal electrically coupled to the terminal of the implant assembly. If a return electrode is provided on the implant assembly, the medical system may be configured in one of two manners. In one example, the medical system further comprises a ground electrode separate from the return electrode, in which case, the power supply has another terminal electrically coupled to the ground electrode. In another example, the implant assembly has another terminal in electrical communication with the return electrode, in which case, the power supply has another terminal electrically coupled to the other terminal of the implant assembly. In an optional embodiment, the medical system further comprises a delivery catheter configured for slidably receiving the implant assembly.

In accordance with still another aspect of the present inventions, an implant assembly comprises an elongated pusher member, and an implantable device (e.g., a vaso-occlusive device) mounted to the distal end of the pusher member. The implant assembly further comprises an electrolytically severable joint disposed on the pusher member, wherein the implantable device detaches from the pusher member when the severable joint is severed. The implant assembly further comprises a terminal carried by the proximal end of the pusher member in electrical communication with the severable joint. In one embodiment, the pusher member comprises an electrically conductive stiffening member through which the terminal and the severable joint are in electrical communication.

The implant assembly further comprises a return electrode carried by the distal end of the pusher member. In one embodiment, the return electrodes takes the form of a coil disposed about the pusher member. The return electrode is electrically isolated from the severable joint and is configured to remain with the pusher member when the severable joint is severed. Although the present inventions should not be so limited in their broadest aspects, the return electrode need not be composed of more expensive and electrically limiting biocompatible materials suitable for chronic implantation, since the return electrode remains with the pusher member. In one embodiment, the implant assembly further comprises another terminal carried by the proximal end of the pusher member in electrical communication with the return electrode. In another embodiment, the terminal in electrical communication with the severable joint is the only terminal carried by the proximal end of the pusher member.

In accordance with yet another aspect of the present inventions, a medical system comprises an implant assembly that includes an elongated pusher member, an implantable device mounted to the distal end of the pusher member, an electrolytically severable joint disposed on the pusher member, wherein the implantable device detaches from the pusher member when the severable joint is severed, and a return electrode carried by the distal end of the pusher member. The detailed features of the implant assembly can be similar to those described above. The medical system further comprises an electrical power supply having a terminal electrically coupled to the severable joint; for example, via a terminal carried by the proximal end of the pusher member and/or an electrically conductive stiffening member of the pusher member.

In accordance with yet another aspect of the present inventions, a method of implanting a medical device (e.g., a vaso-occlusive device) within a patient is provided. The method comprises introducing the medical device within the patient via a pusher member (e.g., through a delivery catheter), conveying electrical energy (e.g., direct electrical current) to a joint disposed on the pusher member, and conveying electrical energy from a return electrode carried by the pusher member (e.g., a coil disposed about the pusher member) to induce an electrolytic reaction between the joint and the return electrode. As a result of the electrolytic reaction, the joint is severed to detach the medical device from the pusher member at a target site (e.g., an aneurismal sac) within the patient. The return electrode remains with the pusher member when the joint is severed. The electrical energy may be conveyed to the joint via the pusher member, and the electrical energy may be conveyed from the return electrode via the pusher member or from the return electrode to a ground electrode via the tissue of the patient. In one method, the pusher member is removed from the patient.

In accordance with yet another aspect of the present inventions, an implant assembly comprises an elongated pusher member, and an implantable device (e.g., a vaso-occlusive device) mounted to the distal end of the pusher member. The implant assembly further comprises an electrolytically severable joint disposed on the pusher member, wherein the implantable device detaches from the pusher member when the severable joint is severed. The implant assembly further comprises a terminal carried by the proximal end of the pusher member in electrical communication with the severable joint. In one embodiment, the pusher member comprises an electrically conductive stiffening member through which the terminal and the severable joint are in electrical communication.

The implant assembly further comprises a return electrode carried by the distal end of the pusher member, and electrically isolated from the severable joint. The return electrode may be carried by the pusher member in such a manner that it remains with the implantable device or remains the pusher member when the severable joint is severed.

The implant assembly further comprises an electrically insulative sheath (e.g., one composed of a polymeric material) fixably coupled to the pusher member and circumferentially surrounding the severable joint and the return electrode. In one embodiment, the return electrode circumferentially extends around the severable joint, and the insulative sheath is disposed about the return electrode. In this case, the return electrode may be, e.g., a coil or a continuous cylinder. The implant assembly may comprise an electrically insulative spacer mounted to the distal end of the pusher member to prevent contact between the severable joint and the return electrode.

In one embodiment, the insulative sheath is configured to prevent diffusion of an electrolyte from a detachment region between the severable joint and the return electrode. In this manner, the electrically insulative sheath may maintain the ideal electrolytic environment within the detachment region between the severable joint and the return electrode in order to facilitate detachment of the implant assembly. In one embodiment, one or both of the severable joint and the return electrode has a hydrophilic coating, so as to, e.g., facilitate wicking of an electrolyte within the detachment region when desired.

In accordance with yet another aspect of the present inventions, a medical system comprises an implant assembly that includes an elongated pusher member, an implantable device mounted to the distal end of the pusher member, an electrolytically severable joint disposed on the pusher member, wherein the implantable device detaches from the pusher member when the severable joint is severed, a return electrode carried by the distal end of the pusher member, and an electrically insulative sheath fixably coupled to the pusher member and circumferentially surrounding the severable joint and the return electrode. The detailed features of the implant assembly can be similar to those described above in other embodiments. The medical system further comprises an electrical power supply having terminal electrically coupled to the severable joint; for example, via a terminal carried by the proximal end of the pusher member and/or an electrically conductive stiffening member of the pusher member.

In accordance with still another aspect of the present inventions, a method of implanting a medical device (e.g., a vaso-occlusive device) within a patient using a pusher member is provided. A joint is disposed on the pusher member and a return electrode is carried by the pusher member. The method comprises introducing an electrolyte within a detachment region between the joint and the return electrode. For example, the electrolyte may be wicked into the detachment region. In one method, the electrolyte is introduced within the detachment region before the medical device is introduced into the patient.

The method further comprises introducing the medical device within the patient via a pusher member (e.g., through a delivery catheter), and substantially preventing the electrolyte from being diffused away from the detachment region using an electrically insulative sheath. In one embodiment, the insulative sheath is fixably coupled to the pusher member. The method further comprises conveying electrical energy (e.g., direct electrical current) to a joint disposed on the pusher member, and conveying electrical energy from a return electrode carried by the pusher member (e.g., a coil disposed about the pusher member) to induce an electrolytic reaction between the joint and the return electrode. As a result of the electrolytic reaction, the joint is severed to detach the medical device from the pusher member at a target site (e.g., an aneurismal sac) within the patient. In one method, the pusher member is removed from the patient.

In accordance with yet another aspect of the present inventions, a medical system comprises an implant assembly that includes an elongated pusher member, an implantable device (e.g., a vaso-occlusive device) mounted to the distal end of the pusher member, and an electrolytically severable joint disposed on the pusher member, wherein the implantable device detaches from the pusher member when the severable joint is severed. The medical system further comprises an electrical power supply coupled to the implant assembly, the power supply configured for conveying pulsed electrical energy (e.g., direct electrical current) to the severable joint. By way of non-limiting example, the pulsed electrical energy may have a duty cycle within the range of 5 percent to 20 percent, and a frequency in the range of 5 KHz to 20 KHz. Pulsing the electrical energy delivered to the severable joint will tend to decrease the detachment time and increase the reliability, repeatability, and uniformity of the detachment process.

In one embodiment, the implant assembly further comprises a terminal carried by the proximal end of the pusher member in electrical communication with the severable joint, wherein the terminal of the power supply is electrically coupled to the terminal of the implant assembly. In another embodiment, the power supply has another terminal electrically coupled to a return electrode, which may be carried by the pusher member. The terminals of the power supply have different electrical potentials.

In one embodiment, the power supply includes a constant current source for conveying the electrical energy, e.g., at an amplitude within the range of 0.25 mA to 10 mA. In another embodiment, the power supply includes a constant voltage source for conveying the electrical energy, e.g., at an amplitude within the range of 0.5V to 11V. In an optional embodiment, the power supply includes a constant current source, a constant voltage source, and a controller configured for initially conveying the electrical energy from the constant current source, and subsequently conveying the electrical energy from the constant voltage source. In another embodiment, the medical system comprises a delivery catheter configured for slidably receiving the implant assembly.

In accordance with a further aspect of the present inventions, a method of implanting a medical device (e.g., a vaso-occlusive device) within a patient is provided. The method comprises introducing the medical device within the patient via a pusher member (e.g., through a delivery catheter), and conveying pulsed electrical energy (e.g., direct electrical current) to a joint disposed on the pusher member to induce an electrolytic reaction at the joint. By way of non-limiting example, the pulsed electrical energy may have a duty cycle within the range of 5 percent to 20 percent, and a frequency in the range of 5 KHz to 20 KHz. As a result of the electrolytic reaction, the joint is severed to detach the medical device from the pusher member at a target site (e.g., an aneurismal sac) within the patient.

In one method, the electrical energy is conveyed to the joint via the pusher member. An optional method comprises conveying pulsed electrical energy from a return electrode (e.g., one carried by the pusher member) to induce the electrolytic reaction between the joint and the return electrode. In one method, the electrical energy is conveyed to the joint from a constant current source, e.g., one having an amplitude within the range of 0.25 mA to 10 mA. In another method, the electrical energy is conveyed to the joint from a voltage source, e.g., one having a voltage within the range of 0.5V to 11V. In an optional method, the pulsed electrical energy is initially conveyed to the joint from a constant current source, and subsequently conveyed to the joint from a constant voltage source. In another method, the pusher member is removed from the patient.

In accordance with still further aspects of the present inventions, a medical system is provided, which comprises an implant assembly that includes an elongated pusher member, an implantable device (e.g., a vaso-occlusive device) mounted to the distal end of the pusher member, and an electrolytically severable joint disposed on the pusher member, wherein the implantable device detaches from the pusher member when the severable joint is severed. The medical system further comprises an electrical power supply coupled to the implant assembly. The power supply includes a constant current source (e.g., one having an amplitude in the range of 0.25 mA to 10 mA), a constant voltage source (e.g., one having an amplitude in the range of 0.5V to 11V), and a controller configured for conveying electrical energy from the constant current source to the severable joint (e.g., for a time period in the range of 0.5 seconds to 1 second), and subsequently conveying electrical energy from the constant voltage source to the severable joint. The electrical energy may be, e.g., direct electric current.

The initial electrical energy from the constant current source may quickly break through the oxide layer on the severable joint, whereas the electrical energy from the constant voltage source may minimize bubbling at the detachment region, thereby decreasing the detachment time and increasing the reliability, repeatability, and uniformity of the detachment process.

In one embodiment, the implant assembly further comprises a terminal carried by the proximal end of the pusher member in electrical communication with the severable joint, wherein the terminal of the power supply is electrically coupled to the terminal of the implant assembly. In another embodiment, the power supply has another terminal electrically coupled to a return electrode, which may be carried by the pusher member. The terminals of the power supply have different electrical potentials. In another embodiment, the medical system comprises a delivery catheter configured for slidably receiving the implant assembly.

In accordance with a yet another aspect of the present inventions, a method of implanting a medical device (e.g., a vaso-occlusive device) within a patient is provided. The method comprises introducing the medical device within the patient via a pusher member (e.g., through a delivery catheter), conveying electrical energy from a constant current source to a joint disposed on the pusher member to degrade an oxide layer on the joint, and subsequently conveying electrical energy from a constant voltage source to the joint to induce an electrolytic reaction at the joint. The electrical energy may be, e.g., direct electrical current. As a result of the electrolytic reaction, the joint is severed to detach the medical device from the pusher member at a target site (e.g., an aneurismal sac) within the patient.

In one method, the electrical energy is conveyed to the joint via the pusher member. An optional method comprises conveying electrical energy from a return electrode (e.g., one carried by the pusher member) to induce the electrolytic reaction between the joint and the return electrode. In another method, the pusher member is removed from the patient.

Other and further aspects and features of the invention will be evident from reading the following detailed description of the preferred embodiments, which are intended to illustrate, not limit, the invention.

BRIEF DESCRIPTION OF DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which:

FIG. 5 is a cross-sectional view of one embodiment a bipolar implant assembly that can be used in the medical system of FIG. 1;

FIG. 6 is a cross-sectional view of one embodiment a monopolar implant assembly that can be used in the medical system of FIG. 2;

FIG. 7 is a cross-sectional view of another embodiment a bipolar implant assembly that can be used in the medical system of FIG. 1;

FIG. 8 is a cross-sectional view of another embodiment a monopolar implant assembly that can be used in the medical system of FIG. 2;

FIG. 9 is a diagram illustrating relative voltage differences in a monopolar arrangements that utilizes an intermediate return electrode;

FIG. 10 is a cross-sectional view of another embodiment a bipolar implant assembly that can be used in the medical system of FIG. 1;

FIG. 11 is a cross-sectional view of still another embodiment a bipolar implant assembly that can be used in the medical system of FIG. 1;

FIG. 12 is a cross-sectional view of yet another embodiment a bipolar implant assembly that can be used in the medical system of FIG. 1.

DETAILED DESCRIPTION OF THE ILLUSTRATED EMBODIMENTS

Figure 1:
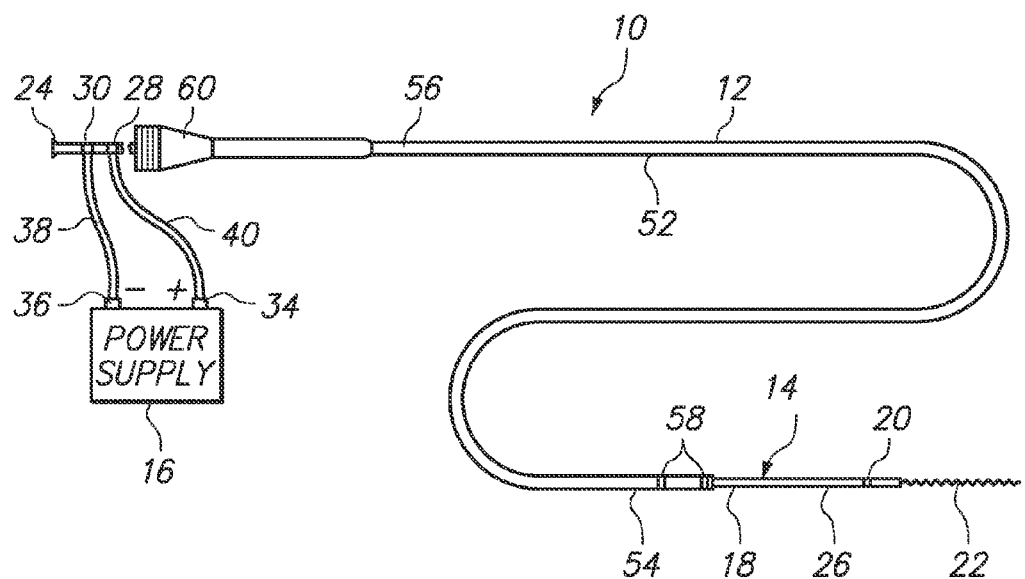
FIG. 1 is a plan view of a medical system arranged in accordance with one embodiment of the present invention, wherein the medical system particularly delivers a vaso-occlusive device into a patient using a bipolar electrolytic delivery means.
Figure 2:
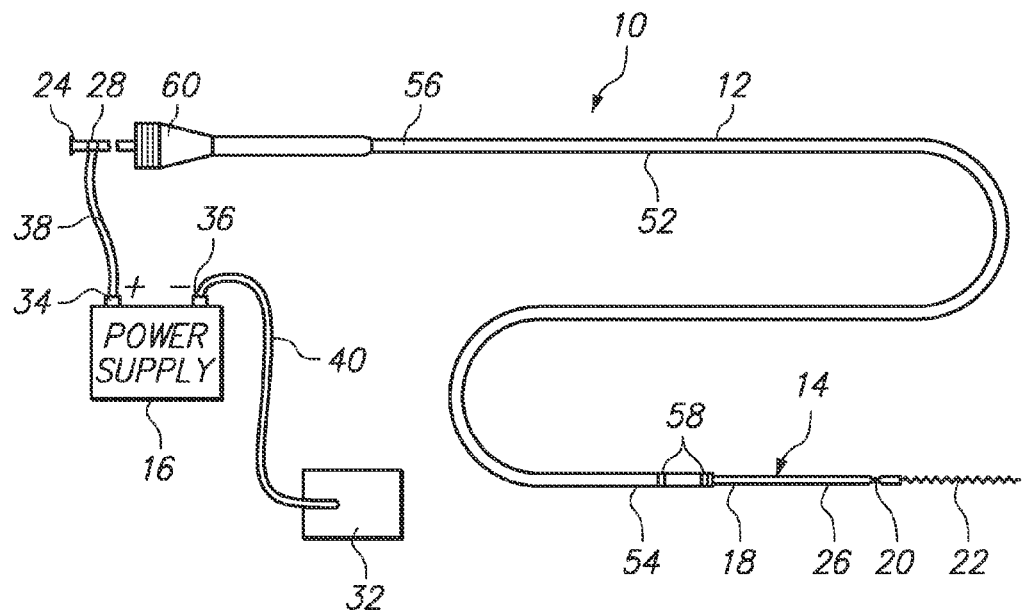
FIG. 2 is a plan view of a medical system arranged in accordance with another embodiment of the present inventions, wherein the medical system particularly delivers a vaso-occlusive device into a patient using a monopolar electrolytic delivery means.

Referring generally to FIGS. 1 and 2, a medical system 10 constructed in accordance with one embodiment of the present inventions will be described. The medical system 10 is used in vascular and neurovascular indications, and particularly in the treatment of aneurysms, such as cerebral aneurysms. The medical system 10 utilizes an electrolytic detachment means to deploy vaso-occlusive devices, such as helical coils, within an aneurysm. Alternatively, the medical system 10 can be utilized to deploy implantable devices other than vaso-occlusive devices. For example, the medical system 10 can alternatively be used to deploy stents and vena cava filters, which are described in further detail in U.S. Pat. No. 6,468,266, which is expressly incorporated herein by reference.

To this end, the medical system 10 generally comprises a delivery catheter 12 that can be intravenously introduced within a patient to access a target site within the vasculature, an implant assembly 14 that can be slidably disposed within the delivery catheter 12, and an electrical power supply 16 that can supply electrical energy to the implant assembly 14 to effect the electrolytic detachment process.

Various types of implant assemblies 14 will be described herein, all of which include a pusher member 18, an electrolytically severable joint 20, and a detachable vaso-occlusive implant 22 mounted to the distal end of the pusher member 18. As will be described in further detail below, the vaso-occlusive implant 22 detaches from the pusher member 18 when the joint 20 is electrolytically severed.

Some of the implant assemblies 14 described herein use bipolar electrolytic means to detach the vaso-occlusive implant 22 from the pusher member 18 at the severable joint 20, and others use monopolar electrolytic means to detach the vaso-occlusive implant 22 from the pusher member 18 at the severable joint 20. In the bipolar cases (shown specifically in FIG. 1), the implant assembly 14 includes positive and negative terminals 28, 30 disposed on the proximal end 24 of the pusher member 18, and a return (ground) electrode (not shown in FIG. 1) carried by the distal end 26 of the pusher member 18. The positive terminal 28 is electrically coupled to the severable joint 20, whereas the negative terminal 30 is electrically coupled to the return electrode. In the monopolar case (shown specifically in FIG. 2), the implant assembly 14 includes a single terminal 28 disposed on the proximal end 24 of the pusher member 18. In this case, the system 10 includes a return electrode 32 in the form of a ground patch electrode or ground needle electrode, and an optional intermediate return electrode (not shown in FIG. 2) carried by the distal end 26 of the pusher member 18. In either of the monopolar or bipolar arrangements, the severable joint 20 serves as an anode, and the return electrode or ground electrode serves as a cathode.

Notably, because of the close proximity of the severable joint 20 and return electrode in the bipolar case, there is a greater chance that the return electrode will induce gas bubbling that will adversely effect the detachment process. That is, greater volumes of bubbling at the return electrode that can displace electrolyte may be created, thus insulating the return path, and thereby causing a variable return electrode impedance (changing voltage drop at the severable joint 20). As will be described in further detail below, the pusher member 18 can be provided with various features that prevent or minimize such bubbling, so that the full advantages of a bipolar configuration can be achieved. These features can likewise be used in the monopolar configuration as well to reduce the chance of gas bubbling.

The power supply 16 conveys electrical energy to the implant assembly 14 (and in particular, the severable joint 20) and returns electrical energy either from the implant assembly 14 (and in particular, the return electrode) or the ground electrode, to effect the electrolytic detachment of the vaso-occlusive implant 22. To this end, the power supply 16 has a positive terminal 34 configured to mate with the positive terminal 28 of the implant assembly 14 via a cable 38, and a negative terminal 36 configured to mate with the negative terminal 30 of the implant assembly 14 (FIG. 1) or the ground electrode 32 (FIG. 2) via a cable 40. Alternatively, in the case of a monopolar arrangement, the positive terminal 24 of the implant assembly 14 is mated directly to the positive terminal 34 of the power supply 16, and in the case of a bipolar arrangement, the positive and negative terminals 28, 30 of the implant assembly 14 are mated directly to the positive and negative terminals 34, 36 (which may be configured in a front-to-back relationship instead of the side-by-side relationship illustrated in FIG. 2) of the power supply 16. For the purposes of this specification, the terms "positive" and "negative" with respect to a terminal is relative and merely means that the positive terminal has a greater voltage potential than that of the negative terminal.

In a monopolar arrangement, the power supply 16 preferably includes a constant current source (not shown in FIGS. 1 and 2) from which the electrical energy is conveyed. In this manner, the detachment times are not affected by the widely varying tissue impedances between the remotely positioned severable joint 20 and ground electrode 32 amongst different patients. A suitable amplitude range for the constant current source is between 0.25 mA and 10 mA. The bipolar arrangement is particularly advantageous, because the varying tissue impedance will not adversely affect the detachment time due to the close proximity between the severable joint 20 and return electrode. As such, the power supply 16 preferably includes a constant voltage source (not shown in FIGS. 1 and 2), which results in a predictable return path voltage drop that avoids over-driving the voltage at the severable joint 20 (anode), which may otherwise cause gas generation (i.e., bubbling). A suitable amplitude range for the constant voltage source is between 0.5V and 11V.

In either of the bipolar configuration or monopolar configuration, the electrical energy takes the form of continuous direct electrical energy; that is, electrical energy that continually flows in one direction only. In an optional embodiment, the power supply 16 is configured to pulse the direct electrical energy supplied by the constant current source or constant voltage source. It has been discovered that pulsing the electrical energy eliminates or minimizes bubbling at the detachment zone. A suitable frequency range and duty cycle for pulsing the electrical energy is 5 KHz to 20 KHz and 5% to 20%, respectively.

Figure 3:
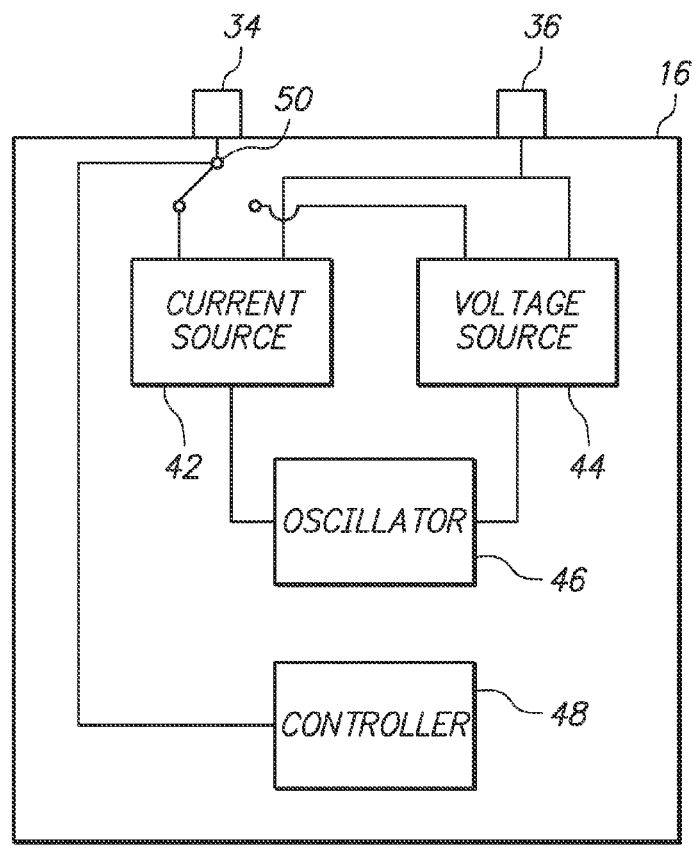
FIG. 3 is a block diagram of an optional power supply that can be used in either of the medical systems of FIGS. 1 and 2.

In an optional embodiment illustrated in FIG. 3, the power supply 16 includes both of a constant current source 42 and a constant voltage source 44 coupled to a radio frequency (RF) oscillator 46, and a controller 48 for initially conveying the electrical energy from the constant current source 42 and subsequently conveying the electrical energy from the voltage current source 44; that is, by selectively coupling the constant current source 42 and constant voltage source 44 to the positive terminal 34 via switch 50. This option works best in a bipolar arrangement, wherein the electrical energy can be delivered from the constant current source 42 to quickly break through the oxide layer on the severable joint 20 for a certain time period (e.g., 0.5 s to 1.0 s), and then the electrical energy can be delivered from the constant voltage source 44 to minimize bubbling at the detachment zone.

Referring back to FIGS. 1 and 2, the delivery catheter 12 includes an elongate, flexible, tubular member 52 composed of a suitable polymeric material and optionally reinforced with a coil or braid to provide strength or obviate kinking propensities. The delivery catheter 12 further includes a lumen (not shown) through which the implant assembly 14 can be selectively located. The delivery catheter 12 further includes a pair of radiopaque markers 58 disposed on the distal end 54 of the tubular member 52 to allow visualization of the delivery catheter 12 relative to the vaso-occlusive implant 22. The delivery catheter 12 further includes a proximal fitting 60 disposed on the proximal end 56 of the tubular member 52 for introduction of the implant assembly 14, as well as for the optional introduction of dyes or treatment materials.

Figure 4:
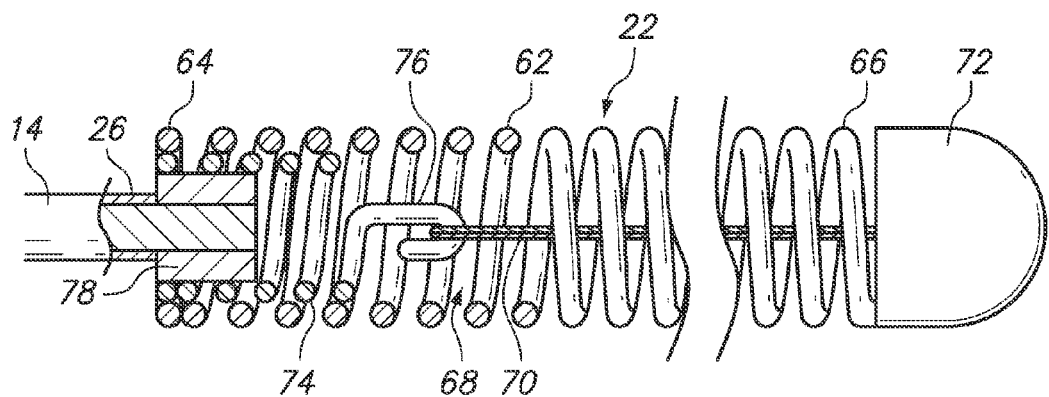
FIG. 4 is a perspective view of one embodiment of a vaso-occlusive device that can be delivered in either of the medical systems of FIGS. 1 and 2.

Referring to FIG. 4, the vaso-occlusive implant 22 is standard and comprises a helically wound primary coil 62 having a proximal end 64, a distal end 66, and a lumen 68 extending therethrough. The materials used in constructing the primary coil 62 may be any of a wide variety of materials, and preferably, a radio-opaque material such as a metal or a polymer. Suitable metals and alloys for the wire making up the coil include super-elastic alloy, such as titanium/nickel alloy, known as "nitinol", or include Platinum Group metals, especially platinum, rhodium, palladium, rhenium, as well as tungsten, gold, silver, tantalum, and alloys of these metals. In addition to being largely biologically inert, these metals have significant radio-opacity and their alloys may be tailored to accomplish an appropriate blend of flexibility and stiffness. Highly preferred is a platinum/tungsten alloy, e.g., 8% tungsten and the remainder platinum.

The primary coil 62 may also be made of radiolucent fibers or polymers (or metallic threads coated with radiolucent or radio-opaque fibers) such as Dacron (polyester), polyglycolic acid, polylactic acid, fluoropolymers (polytetrafluoroethylene), Nylon (polyamide), or even cotton or silk. If a polymer is used as the major component of the primary coil 62, it is desirably filled with some amount of radio-opaque material, such as powdered tantalum, powdered tungsten, bismuth oxide, barium sulfate, and the like.

The primary coil 62 may generally be composed of a wire having a diameter in the range of 0.0025 inches to 0.006 inches, which is then wound into a primary form having a diameter between 0.003 inches and 0.025 inches. But for most neurovascular applications, a diameter between 0.008 to 0.018 inches provides sufficient hoop strength to hold the primary coil 62 in place within the chosen body site, lumen, or cavity, without substantially distending the wall of the site and without moving from the site as a result of the repetitive fluid pulsing found in the vascular system. The axial length of the primary coil 62 will usually fall in the range of 0.5 cm to 100 cm, more usually 2 cm to 40 cm. Depending on the usage, the primary coil 62 may have 10-75 turns per centimeter, preferably 10-40 turns per centimeter. All of the dimensions here are provided only as guidelines, and the invention, when applied to vaso-occlusive devices, should not be limited thereto. Only dimensions that are suitable for use in occluding sites within the human body, however, are included in the scope of this invention as applied to vaso-occlusive devices.

Depending on the desired therapeutic effect and the shape of the site to be treated, the primary coil 62 may later be treated or accessorized in numerous ways in order to enhance its therapeutic effect. The primary coil 62 may be made to form various secondary shapes, often through the use of heat treatment, that may be better suited to fill a particular treatment site, as disclosed in U.S. Pat. Nos. 5,853,418 and 6,280,457, the entireties of which are hereby expressly incorporated herein by reference. Alternatively, the primary coil 62 may have little or no shape after introduction into the vascular space, as disclosed in U.S. Pat. No. 5,690,666, the entirety of which is hereby expressly incorporated herein by reference. In addition, external materials may be added to the outside of the primary coil 62 in an effort to increase its thrombolytic properties. These alternative embodiments are disclosed in U.S. Pat. Nos. 5,226,911; 5,304,194; 5,549,624; and 5,382,259; the entireties of which are hereby expressly incorporated herein by reference, and 6,280,457, the entirety of which has previously been incorporated by reference.

The vaso-occlusive implant 22 further includes a stretch-resisting filament 70, which extends through the coil lumen 68 and is secured to the primary coil 62 at two locations to prevent axial stretching of the primary coil 62 in the event that the pusher member 18 must be withdrawn or repositioned to change the position of the vaso-occlusive implant 22. Specifically, the proximal and distal ends of the stretch-resisting filament 70 are respectively affixed to the proximal and distal ends 64, 66 of the primary coil 62. Alternatively, the stretch-resisting filament 70 only extends through a portion of the lumen 68 and is attached to the primary coil 62 at a location between the proximal and distal ends 64, 66 of the primary coil 62.

The distal end of the stretch-resisting filament 70 may be secured to the primary coil 62 by melting, gluing, or otherwise fixedly attaching the stretch-resisting filament 70 to the primary coil 62, either at the distal end 66 or some location between the proximal and distal ends 64, 66 of the primary coil 62. In the illustrated embodiment, the distal end of the stretch-resisting filament 70 is glued or melted and reformed into a distal cap 72, the diameter of which is larger than the inner diameter of the primary coil 62. Alternatively, the stretch-resisting filament 70 may be tied in a knot (not shown), which may or may not be attached to the primary coil 62. These methods of attachment are disclosed in more detail in U.S. Pat. No. 5,582,619, the entirety of which is hereby expressly incorporated herein by reference.

In a preferred embodiment, the stretch-resisting filament 70 is fibrous and desirably polymeric. Suitable polymeric materials can be either thermosetting or thermoplastic and can comprise a bundle of threads or a single filament. Thermoplastics are preferred because they allow simplification of the procedure for constructing the assembly, since they may be melted and formed into the distal cap 72. Simple tools, such as soldering irons, may be used to form the distal cap 72. Thermosetting plastics would typically be held in place by an adhesive. Suitable polymers include most biocompatible materials that may be made into fibers, including thermoplastics, e.g., polyesters such as polyethyleneterephthalate (PET), especially Dacron; polyamides, including the Nylons; polyolefins, such as polyethylene, polypropylene, polybutylene, their mixtures, alloys, block, and random copolymers; polyglycolic acid; polylactic acid; fluoropolymers (polytetrafluoroethylene) or even silk or collagen. The stretch-resisting polymer may be made from materials used as dissolvable sutures, for instance, polylactic acid or polyglycolic acid, to encourage cell growth in the aneurysm after their introduction. Highly preferred is polypropylene, for instance, in the form of 10-0 and 9-0 polypropylene suture material. The diameter of the polymer is typically between about 0.0001 inches and about 0.01 inches.

The vaso-occlusive implant 22 further includes an anchor coil 74 coaxially situated in the coil lumen 68. The anchor coil 74 is preferably soldered or welded to the inner surface of the primary coil 62. In the illustrated embodiment, the anchor coil 74 is preferably less than 2.6 mm long, preferably about 1.0 mm long. The anchor coil 74 has a distal hook 76 to which the stretch-resisting filament 70 is attached. The anchor coil 74 may be composed of the same material as the primary coil 62. The vaso-occlusive implant 22 further includes a polymeric plug 78 that is slipped over the distal end of the pusher member 18 and into the proximal end 64 of the primary coil 62. The assembled joint is then heated, so as to allow the thermoplastic of the polymeric plug 78 to flow and secure the primary coil 62 to the pusher member 18.

Referring now to FIG. 5, one embodiment of a bipolar implant assembly 14(1) will now be described. The bipolar implant assembly 14(1) comprises the previously described vaso-occlusive implant 22 and a pusher member 18(1). The pusher member 18(1) comprises an elongated stiffening member 80, which includes an electrically conductive coil wire and an electrically insulative coating disposed over the core wire. The core wire of the stiffening member 80 can be composed of any suitable electrically conductive and rigid material, such as stainless steel, and the coating can be composed of any suitable electrically insulative material, such as polyimide, polytetrafluoroethylene (PTFE), tetrafluoroethylene (TFE), polyparaxylxylene (e.g., Parylene), polyethyleneterephthalate (PET), polybutyleneterephthalate (PBT), cyanoacrylate adhesives, or other suitable insulating layer.

In the illustrated embodiment, the stiffening member 80 tapers from a large diameter section 81 to a small diameter section 83. The core wire of the stiffening member 80 can be ground to effect this taper. In the illustrated embodiment, the diameter of the core wire in the large diameter section 81 of the stiffening member 80 is 0.004 inches, and the diameter of the core wire in the small diameter section 83 is 0.0025 inches. The insulative coating may have a suitable thickness (e.g., 0.00035 inches). Notably, the large diameter section 81 of the stiffening member 80 provides the pusher member 18(1) with lateral rigidity, as well as tensile strength, whereas the small diameter section 83 of the stiffening member 80 provides the pusher member 18(1) with the desired lateral flexibility adjacent the vaso-occlusive implant 22 to minimize kickback during detachment of the vaso-occlusive implant 22.

A distal region of the core wire at the small diameter section 83 is either not coated with the insulative coating or a portion of the insulative coating is removed (e.g., using laser ablation) to expose a portion of the core wire, thereby forming the electrolytic severable joint 20, which serves as the anode of the bipolar implant assembly 18(1). Preferably, the length of the severable joint 20 is relatively short (e.g., 0.002 inches). As a result, the severable joint 20 has a narrow range of circumferential contact with the electrolyte, so that the dissolution of the core wire will be limited to a narrow circumferential band, rather than a broad one, thereby resulting in a quicker erosion through the thickness of the core wire.

The pusher member 18(1) further comprises an electrically conductive coil that serves as a return electrode 86 (i.e., the cathode of the bipolar implant assembly 18(1)). The return electrode coil 86 may be formed by winding a wire having a suitable diameter (such as, e.g., 0.00175 inches) around a mandrel. The return electrode coil 86 has suitable dimensions; for example, an inner diameter of 0.006 inches (and thus, an outer diameter of 0.0095 inches) and a length of 0.75 mm. In the illustrated embodiment, a length of the wire forming the return electrode coil 86 is not wound, so as to make a straight tail 88 for coupling to an electrical conductor, as will be described in further detail below. The return electrode coil 86 circumferentially extends around the severable joint 20 and is spatially isolated from the severable joint 20 via a spacer element 90 mounted to the stiffening member 80 at a location proximal to the severable joint 20 using a suitable adhesive. The return electrode coil 86 may be composed of a suitable electrically conductive material, such as silver or copper. In the illustrated embodiment, the spacer element 90 takes the form of a coil coated with an electrically insulative material, such as, e.g., such as polyimide, PTFE, TFE, Parylene, PET, PBT, cyanoacrylate adhesives, or other suitable insulating layer. Alternatively, the spacer element 90 may take the form of a tube composed of an electrically insulative material, such as, e.g., polyetheretherketone (PEEK).

Significantly, while the stiffening member 80 serves as a tensioning element during deployment and retraction of the vaso-occlusive implant 22, the return electrode coil 86 serves as a compression element, while allowing the distal end of the pusher member 18(1) to remain laterally flexible. Thus, when loading the vaso-occlusive implant 22 in axial compression (such as during deployment), the return electrode coil 86 can compress against a structure distal to the severable joint 20, thereby avoiding compression loading of the detachment zone, and thus reducing any possibility of kinking, fatiguing, or otherwise damaging the severable joint 20 prior to detachment.

In the illustrated embodiment, the return electrode coil 86 is composed of silver with a thick layer of silver chloride, which results in a high total charge capacity per unit length of wire. This feature provides a facile solid to liquid phase electrochemical reaction that does not evolve gaseous bubbles. The electrochemical reaction occurs at a very low bias voltage and is relatively insensitive to magnitude of electrical current. Thus, the return electrode coil 86 can be placed closer to the severable joint 20 without introducing gaseous bubbles, which as discussed above, can insulate the detachment zone from electrolytes needed for the electrochemical reaction, thereby prolonging detachment of the vaso-occlusive implant 22.

The electrochemical reaction at the return electrode coil 86 with the electrolyte, such as sodium chloride, releases chlorine ions into the electrolyte in accordance with the equation: $AgCl(s)+1e^-\rightarrow Ag(s)+Cl^-(aq)$, $E^0=0.22$ V HSE. This electrochemical reaction requires low voltage, has rapid charge transfer, and results in fast ion diffusion. Silver chloride has the unusual property of being minimally soluble in water, with the chloride released from the return electrode coil 86 being drawn to the severable joint 20. Notably, in the illustrated embodiment, the severable joint 20 is composed of stainless steel (i.e., iron, chrome, and nickel). The resulting iron chloride, nickel chloride, and chrome chloride hexahydrate is highly soluable in water. The electrochemical reaction at the severable joint 20 releases iron into the electrolyte, thereby dissolving the severable joint 20 in accordance with the equations: $Fe(s)-2e^-$, $Fe(s)-3e^-\rightarrow Fe^{2+}(s)$, $Fe^{2+}(s)$; $Fe^{2+}(s)+2Cl^-(aq)\rightarrow FeCl_2(aq)$.

The return electrode coil 86 can be chloridized in any suitable manner. In one embodiment, the return electrode coil 86 is composed of pure silver, which is chloridized by placing it in a saline solution while the windings are stretched to 50-100% open pitch. The return electrode coil 86 is connected to a power supply, and a suitable electrode current (e.g., 0.1 mA) is conveyed between the coil 86 as an anode and a return electrode as a cathode for a suitable period of time (e.g., 10 minutes). The open pitch of the return electrode coil 86 will naturally close when an outer sheath (described below) is heat shrunk over the coil 86.

The pusher member 18(1) further comprises a radiopaque marker, and in particular a platinum marker coil 92, circumferentially extending around the stiffening member 80 just proximal to the return electrode coil 86. The marker coil 92 may be formed by winding a wire having a suitable diameter (e.g., 0.002 inches) around a mandrel. The marker coil 92 has suitable dimensions; for example, an inner diameter of 0.005 inches (and thus, an outer diameter of 0.009 inches) and a length of 3.0 mm. The marker coil 92 may have an open pitch (e.g., 10%) to increase its lateral flexibility. The marker coil 92 is bonded to the stiffening member 80 using a suitable adhesive.

Prior to such bonding, the tail 88 of the return electrode coil 86 is proximally threaded through the lumen of the marker coil 92 and connected to an electrical conductor 94 via suitable means, such as soldering or welding, or bonding using an electrically conductive adhesive, such as a silver-filled epoxy. The electrical conductor 94 may be a copper or silver wire that is coated with an electrically insulative material, such as, e.g., polyimide, to ensure electrical isolation of the electrical conductor 94 from the stiffening member 80, and thus, electrical isolation between the return electrode coil 86 and the severable joint 20. The electrical conductor 94 has suitable dimensions, such as, e.g., a wire diameter of 0.0015 inches and a total diameter (including insulation) of 0.002 inches.

The pusher member 18(1) further comprises an electrically insulative sheath 96 disposed over the assembly, including the return electrode coil 86, marker coil 92, and the stiffening member 80. The sheath 96 may be composed of a suitable polymeric material, such as PTFE or TFE, and have suitable dimensions (e.g., a wall thickness of 0.002 inches and an inner diameter of 0.006 inches). In the illustrated embodiment, the sheath 96 is heat shrunk over the assembly.

Significantly, the sheath 96 circumferentially surrounds both the severable joint 20 and the return electrode coil 86. In addition to providing the distal end of the pusher member 18(1) with an increased compressive strength (along with the return electrode coil 86), the existence of the sheath 96 reduces the possibility of previously-deployed vaso-occlusive devices from short-circuiting the severable joint 20, which can prolong detachment time. In addition, the sheath 96 tends to exclude bodily fluids (e.g., blood) from the interior of the pusher member 18(1), thereby reducing diffusion and convection of an ideal electrolytic environment away from the detachment region when the implant assembly 14 is exposed to the bodily fluids. The ideal electrolytic environment can be created by introducing an ideal electrolyte, such as a sodium chloride solution (saline) into the detachment region, for example, by soaking the distal end of the implant assembly 14 within the saline prior to introduction of the implant assembly 14 into the delivery catheter 12.

To facilitate wicking of the saline into the detachment zone, a hydrophilic coating can be applied to one or both of the severable joint 20 and return electrode coil 86 as a rehydratable gel or water soluble polymer, such as polyvinyl alcohol. Preferably, the hydrophilic coating is weakly anchored to the severable joint 20 so as not to hinder detachment of the vaso-occlusive device 22. Thus, in spite of the sheath 96 substantially isolating the detachment region from the exterior environment, the hydrophilic quality of the detachment region allows liquid to wick into the detachment zone upon soaking of the implant assembly 14(1) in the liquid. In an optional embodiment, the hydrophilic material may comprise of, or contain, readily soluble salt or salts, such as sodium chloride, other metal chloride, metal chlorate, or metal sulfate. In the presence of water, these salt(s) dissolve, providing an ion-rich electrolyte that accelerates electrochemical reaction and dissolution at the severable joint 20. In this optional case, the implant assembly 14 need not be soaked in the electrolytic solution, but rather water, since the electrolytic solution is created within the detachment region as the water makes contact with the severable joint 20 and/or return electrode coil 86.

The pusher member 18(1) further comprises an electrically conductive hypotube 98 composed of a suitable electrically conductive material, such as stainless steel. The core wire in the proximal end of the stiffening member 80 is exposed and is bonded to the interior of the hypotube 98 using a suitable electrically conductive bonding material, such as, e.g., silver-filled epoxy. The distal end of the hypotube 98 abuts the proximal end of the sheath 96. The hypotube 98 may have suitable dimensions, e.g., an outer diameter of 0.012 inches, and an inner diameter of 0.006 inches. Thus, any portion of the hypotube 98 forms the positive terminal 28 (shown in FIG. 1) that electrically communicates with the severable joint 20 via a forward electrical path that includes the core wire of the stiffening member 80.

The pusher member 18(1) further comprises another electrically insulative sheath 100 disposed over a portion of the hypotube 98, and an electrically conductive terminal coil 102, which serves as the negative terminal 30 (shown in FIG. 1), mounted around the insulative sheath 100. The insulative sheath 100 may be composed of a suitable polymeric material, such as PTFE or TFE, and have suitable dimensions (e.g., a wall thickness of 0.002 inches and an inner diameter of 0.006 inches). In the illustrated embodiment, the insulative sheath 100 is heat shrunk over the hypotube 98. The terminal coil 102 may be composed of a material, such as platinum, and is electrically coupled to the return electrode coil 86 via a return electrical path that includes the electrical conductor 94 and the tail 88 of the return electrode coil 86.

To this end, the electrical conductor 94, which is connected to the return electrode coil 86 via the tail 88, is proximally threaded through the hypotube 98, and distally bent about the proximal end of the hypotube 98, so that the proximal end of the electrical conductor 94 can be placed between the insulative sheath 100 and the terminal coil 102. Preferably, the electrical conductor 94 is disposed on the insulative sheath 100, and then the terminal coil 102 is bonded over the electrical conductor 94 and insulative sheath 100 using soldering or welding or an electrically conductive adhesive, such as, e.g., silver-filled epoxy.

Referring now to FIG. 6, one embodiment of a monopolar implant assembly 14(2) will now be described. The monopolar implant assembly 14(2) comprises the previously described vaso-occlusive implant 22 and a pusher member 18(2). The pusher member 18(2) comprises an elongated stiffening member 180 that includes an uninsulated electrically conductive core wire. The core wire of the stiffening member 180 can be composed of any suitable electrically conductive and rigid material, such as stainless steel. In the illustrated embodiment, the stiffening member 180 comprises a proximal section 185 and a distal section 187 that are coupled together via a crimped bushing 189. Alternatively, the proximal section 185 and distal section 187 of the stiffening member 180 can be soldered or welded together. The core wire of the distal section 187 may have a uniform diameter equal to the smallest diameter of the proximal section 185.

In the illustrated embodiment, the stiffening member 180 tapers from a large diameter section 181 to a small diameter section 183. The core wire of the stiffening member 180 can be ground to effect this taper. In the illustrated embodiment, the diameter of the core wire in the large diameter section 181 of the stiffening member 180 is 0.010 inches, and the diameter of the core wire in the small diameter section 183 is 0.0025 inches.

Like the previously described stiffening member 80, the large diameter section 181 of the stiffening member 180 provides the pusher member 18(2) with lateral rigidity, as well as tensile strength, whereas the small diameter section 183 of the stiffening member 180 provides the pusher member 18(2) with the desired lateral flexibility adjacent the vaso-occlusive implant 22 to minimize kickback during detachment of the vaso-occlusive implant 22.

The formation of the electrolytic severable joint 20, which serves as the anode of the monopolar implant assembly 14(2), can be the same as that described above with respect to the pusher member 18(1). Any portion of the larger diameter section 181 of the stiffening member 180 can serve as the positive terminal 28 (illustrated in FIG. 2) that electrically communicates with the severable joint 20 via a forward electrical path that includes the core wire of the stiffening member 180.

The pusher member 18(2) further comprises an electrically conductive coil 186 that serves as an intermediate return electrode; that is, a return electrode between the severable joint 20 and the ground electrode 32 (shown in FIG. 2). The return electrode coil 186 may be formed by winding a wire having a suitable diameter (such as, e.g., 0.00175 inches) around a mandrel. The return electrode coil 186 has suitable dimensions; for example, an inner diameter of 0.006 inches and a length of 0.75 mm. The return electrode coil 186 circumferentially extends around the severable joint 20 and is spatially isolated from the severable joint 20 via a spacer element 190 mounted to the stiffening member 180 at a location proximal to the severable joint 20 using a suitable adhesive. The return electrode coil 186 may be composed of a suitable electrically conductive material, such as silver or copper. The spacer element 190 may take the same form and be constructed of the same materials as the spacer element 90 described above.

Like the previously described return electrode 86, the return electrode coil 186 serves as a compression element and may be coated with a layer of silver chloride to further prevent or reduce the generation of gaseous bubbles. Unlike the previously described return electrode 86, the return electrode coil 186 is not electrically coupled to a terminal. Instead, as illustrated in FIG. 9, two electrochemical circuits are created: one between the severable joint 20 and the return electrode coil 186, and one between the return electrode coil 186 and the ground return electrode 32. The large surface area of the return electrode coil 186 provides an electrochemical circuit with a lower impedance return path to ground than the electrolyte itself. When a voltage is applied between the severable joint 20 and the ground return electrode 32, the return electrode coil 186 will be at a voltage in between the severable joint 20 and the ground return electrode 32, as illustrated in FIG. 9. Thus, the return electrode coil 186 shortens the diffusion distance for metal ions and provides a reducing surface that can plate these ions out of the electrolyte, thus lowering metal ion concentration at the detachment region. This increases the rate of metal ion dissolution and reduces the magnitude of over-voltage required. This, in turn, reduces bubbling at the detachment region, thereby shortening the detachment time and making the detachment process more reliable.

The pusher member 18(2) further comprises a radiopaque marker, and in particular a platinum marker coil 192, circumferentially extending around the stiffening member 80. The marker coil 192 may be formed by winding a wire having a suitable diameter (e.g., 0.002 inches) around a mandrel. In the illustrated embodiment, the distal end of the marker coil 192 is disposed within the proximal end of the return electrode coil 186. To this end, the inner diameter of the marker coil 192 can be 0.002 inches (and thus, an outer diameter of 0.006 inches) and a length of 3.0 mm. Like the previously described marker coil 92, the marker coil 192 may have an open pitch (e.g., 10%) to increase its lateral flexibility, and may be bonded to the stiffening member 80 using a suitable adhesive, such as epoxy. The inner surface of the return electrode coil 186 may be bonded to the outer surface of the marker coil 192 using a suitable adhesive, such as epoxy.

The pusher member 18(2) further comprises an electrically insulative sheath 196 disposed over the assembly, including the return electrode coil 186, marker coil 192, and the stiffening member 180. The sheath 196 may be composed of a suitable polymeric material, such as PTFE or TFE, and have suitable dimensions (e.g., a wall thickness of 0.002 inches and an inner diameter of 0.006 inches). In the illustrated embodiment, the sheath 196 is heat shrunk over the assembly.

Significantly, the sheath 196 circumferentially surrounds both the severable joint 20 and the return electrode coil 186. Thus, like the previously described sheath 96 of the bipolar pusher member 18(1), the sheath 196 increases the compressive strength of the pusher member 18(2), and reduces diffusion and convection of an ideal electrolytic environment away from the detachment region when the implant assembly 14(2) is exposed to the bodily fluids. As previously described, such ideal electrolytic environment can be created by introducing the ideal electrolyte into the detachment region or introducing water into the detachment region previously coated with salt. To facilitate wicking of the saline or water into the detachment zone, a hydrophilic coating can be applied to one or both of the severable joint 20 and return electrode coil 186 in the same manner previously described above.

Referring now to FIG. 7, another embodiment of a bipolar implant assembly 14(3) will now be described. The bipolar implant assembly 14(3) differs from the previously described bipolar implant assembly 14(1) in that it includes an exposed detachment region. To this end, the bipolar implant assembly 14(3) comprises the previously described vaso-occlusive implant 22 and a pusher member 18(3). The pusher member 18(3) comprises an elongated stiffening member 280 that includes an electrically conductive core wire and an electrically insulative coating disposed over the core wire. The core wire of the stiffening member 280 can be composed of any suitable electrically conductive and rigid material, such as stainless steel, and the coating can be composed of any suitable electrically insulative material, such as polyimide, PTFE, TFE, Parylene, PET, PBT, cyanoacrylate adhesives, or other suitable insulating layer.

In the illustrated embodiment, the stiffening member 280 tapers from a large diameter section 281 to a small diameter section 283. The core wire of the stiffening member 180 can be ground to effect this taper. In the illustrated embodiment, the diameter of the core wire in the large diameter section 281 of the stiffening member 280 is 0.004 inches, and the diameter of the core wire in the small diameter section 283 is 0.0025 inches.

Like the previously described stiffening member 80, the large diameter section 281 of the stiffening member 280 provides the pusher member 18(3) with lateral rigidity, as well as tensile strength, whereas the small diameter section 283 of the stiffening member 280 provides the pusher member 18(3) with the desired lateral flexibility adjacent the vaso-occlusive implant 22 to minimize kickback during detachment of the vaso-occlusive implant 22. The construction of the core wire, coating, and formation of the electrolytic severable joint 20, which serves as the anode of the bipolar implant assembly 14(3), can be the same as that described above with respect to the pusher member 18(1).

The pusher member 18(3) further comprises an electrically conductive coil 286 that serves as a return electrode (i.e., the cathode of the bipolar implant assembly 14(3). The return electrode coil 286 may be formed by winding a wire having a suitable diameter (such as, e.g., 0.002 inches) around a mandrel. The return electrode coil 286 has suitable dimensions; for example, an inner diameter of 0.003 inches (and thus, an outer diameter of 0.007 inches) and a length of 0.75 mm. In the illustrated embodiment, the return electrode coil 286 has an open pitch (e.g., 20%) to increase its lateral flexibility. The return electrode coil 286 may be composed of a suitable electrically conductive material, such as silver or copper. The return electrode coil 286 circumferentially extends around the stiffening member 280, and in particular, is bonded to the stiffening member 280 at a location proximal to the severable joint 20 using a suitable adhesive, such as epoxy. Like the previous return electrode coil 86, the return electrode coil 286 serves as a compression element and may be coated with a layer of silver chloride to further prevent or reduce the generation of gaseous bubbles.

The pusher member 18(3) further comprises a radiopaque marker, and in particular a platinum marker coil 292, circumferentially extending around the stiffening member 280. The marker coil 292 may be formed by winding a wire having a suitable diameter (e.g., 0.002 inches) around a mandrel. In the illustrated embodiment, the inner and outer diameter of the marker coil 292 is preferably the same as the inner and outer diameter of the return electrode coil 286; that is, an inner diameter of 0.003 inches and an outer diameter of 0.007 inches. The length of the marker coil 292 may be 3.0 mm. Like the previously described marker coil 92, the marker coil 292 may have an open pitch (e.g., 10%) to increase its lateral flexibility, and may be bonded to the stiffening member 80 using a suitable adhesive, such as epoxy.

The pusher member 18(3) further comprises an interconnecting flex coil 295, the proximal end of which is circumferentially disposed around the distal end of the marker coil 292, and the distal end of which is circumferentially disposed around the proximal end of the return electrode coil 286. The flex coil 295 is composed of an electrically conductive material, such as stainless steel, and is suitably bonded to the marker coil 292 and return electrode coil 286 using an electrically conductive adhesive, such as silver-filled epoxy. As such, the marker coil 292 and return electrode coil 286 are electrically coupled together. The flex coil 295 may be formed by winding a wire having a suitable diameter (e.g., 0.00175 inches) around a mandrel. The flex coil 295 has suitable dimensions; for example, an inner diameter of 0.007 inches (and thus, an outer diameter of 0.0105) and a length of 30 mm. In the illustrated embodiment, the flex coil 295 has a closed pitch.

The pusher member 18(3) further comprises an electrical conductor 294 connected to the external surface of the marker coil 292 via suitable means, such as soldering or welding, or bonding using an electrically conductive adhesive, such as silver-filled epoxy. The electrical conductor 292 may be a copper or silver wire that is coated with an electrically insulative material, such as, e.g., polyimide, to ensure electrically isolation of the electrical conductor 292 from the stiffening member 280, and thus, electrical isolation between the return electrode coil 286 and the severable joint 20. The electrical conductor 292 has suitable dimensions, such as, e.g., a wire diameter of 0.0015 inches and a total diameter (including insulation) of 0.002 inches.

The pusher member 18(3) further comprises an electrically insulative sheath 296 disposed over the assembly, including the proximal end of the marker coil 292, the electrical conductor 294, and the portion of the stiffening member 280 extending proximally from the marker coil 292, with the distal end of the sheath 296 abutting the proximal end of the flex coil 295. The sheath 296 may be composed of a suitable polymeric material, such as PTFE or TFE, and have suitable dimensions (e.g., a wall thickness of 0.002 inches and an inner diameter of 0.006 inches). In the illustrated embodiment, the sheath 296 is heat shrunk over the assembly.

The pusher member 18(3) further comprises a first electrically conductive hypotube 298 composed of a suitable electrically conductive material, such as stainless steel. The core wire in the proximal end of the stiffening member 280 is exposed and is bonded to the interior of the hypotube 298 using a suitable electrically conductive bonding material, such as, e.g., silver-filled epoxy. The distal end of the hypotube 298 abuts the proximal end of the sheath 296. The hypotube 298 may have suitable dimensions, e.g., an outer diameter of 0.012 inches, an inner diameter of 0.006 inches, and a length of 150 cm. Thus, any portion of the hypotube 298 forms the positive terminal 28 (shown in FIG. 1) that electrically communicates with the severable joint 20 via the forward electrical path that includes the core wire of the stiffening member 80.

The pusher member 18(3) further comprises a second electrically conductive hypotube 299 composed of a suitable electrically conductive material, such as stainless steel. The proximal end of the electrical conductor 294 is exposed and is bonded to the interior of the hypotube 299 using a suitable electrically conductive bonding material, such as, e.g., silver-filled epoxy. The hypotube 299 may have suitable dimensions, e.g., an outer diameter of 0.012 inches, an inner diameter of 0.006 inches, and a length of 10 mm. Thus, any portion of the hypotube 299 forms the negative terminal 30 (shown in FIG. 1) that electrically communicates with the return electrode coil 286 via return electrical path that includes the electrical conductor 294, marker coil 292, and flex coil 295.

The pusher member 18(3) further comprises a reinforcing mandrel 300 around which the proximal end of the first hypotube 298 and the distal end of the second hypotube 299 is bonded using a suitable adhesive, such as epoxy. The reinforcing mandrel 300 may be a stainless steel wire that is coated with an electrically insulative material, such as, e.g., polyimide, to ensure electrically isolation between the first and second hypotubes 299, 300, and thus, electrical isolation between the severable joint 20 and the return electrode coil 286. The reinforcing mandrel 300 has suitable dimensions, such as, e.g., a wire diameter of 0.004 inches and a length of 10 mm.

Referring now to FIG. 8, another embodiment of a monopolar implant assembly 14(4) will now be described. The monopolar implant assembly 14(4) differs from the previously described monopolar implant assembly 14(2) in that the intermediate return electrode is configured to remain with a vaso-occlusive implant 23 when detached from a pusher member 18(4). As discussed above with respect to the monopolar pusher member 18(2), the large surface area of the intermediate return electrode reduces bubbling at the detachment region.

The vaso-occlusive implant 23 is similar to the previously described vaso-occlusive implant 22 in that it comprises the primary coil 62, stretch resisting filament 70, and distal cap (not shown). The vaso-occlusive implant 23 differs in that it comprises an intermediate return electrode 386 in the form of an electrically conductive hypotube disposed within the proximal end of the primary coil 62. In the illustrated embodiment, the proximal end of the primary coil 62 has an open pitch (e.g., 4 of the proximal turns are open pitched) that is wound around, and mounted to, the intermediate return electrode 386 via suitable means, such as soldering or welding, or bonding using an electrically conductive adhesive, such as silver-filled epoxy. In an alternative embodiment, the intermediate return electrode 386 may take the form of an electrically conductive coil. The intermediate return electrode 386 is preferably composed of a biocompatible material suitable for chronic implantation. Notably, because the primary coil 62 is electrically coupled to the intermediate return electrode 386, the effective surface area of the intermediate return electrode 386 is substantially increased to the extent that the primary coil 62, itself, is electrically conductive, thereby further minimizing the chance of gaseous bubbling.

The pusher member 18(4) comprises an elongated stiffening member 380 that includes an uninsulated electrically conductive core wire. The core wire of the stiffening member 380 can be composed of any suitable electrically conductive and rigid material, such as stainless steel. In the illustrated embodiment, the stiffening member 380 tapers from a large diameter section 381 to a small diameter section 383. The core wire of the stiffening member 380 can be ground to effect this taper. In the illustrated embodiment, the diameter of the core wire in the large diameter section 381 of the stiffening member 380 is 0.010 inches, and the diameter of the core wire in the small diameter section 383 is 0.0025 inches.

Like the previously described stiffening member 80, the large diameter section 381 of the stiffening member 380 provides the pusher member 18(4) with lateral rigidity, as well as tensile strength, whereas the small diameter section 383 of the stiffening member 380 provides the pusher member 18(4) with the desired lateral flexibility adjacent the vaso-occlusive implant 22 to minimize kickback during detachment of the vaso-occlusive implant 22.

The pusher member 18(4) further comprises a radiopaque marker, and in particular a platinum marker coil 392, circumferentially extending around the stiffening member 380. The marker coil 392 may be formed by winding a wire having a suitable diameter (e.g., 0.002 inches) around a mandrel. The marker coil 392 has suitable dimensions; for example, an inner diameter of 0.003 inch and a length of 3.0 mm. The marker coil 392 may have an open pitch (e.g., 10%) to increase the lateral flexibility of the marker coil 392.

The pusher member 18(4) further comprises an electrically insulated coil 395 having an electrically conductive wire and an electrically insulative coating disposed thereon. The insulated coil 395 may be formed by winding a wire having a suitable diameter (e.g., 0.00175 inches) around a mandrel. In the illustrated embodiment, the insulated coil 395 has an open pitch (e.g., 50%) to increase the lateral flexibility of the coil 395. The proximal windings of the insulative coil 395, which are stripped of the insulative coating, are circumferentially mounted around the distal end of the stiffening member 380 via suitable means, such as soldering or welding, or bonding using an electrically conductive adhesive, such as silver-filled epoxy.

The distal end 397 of the insulated coil 395 is straightened and extended through the lumen of the return electrode 386 of the vaso-occlusive device 23. A region of the straight section 397 is either not coated with the insulative material or a portion of the insulative material is removed (e.g., using laser ablation) to expose a portion of the wire, thereby forming the electrolytic severable joint 20. The formation of the electrolytic severable joint 20, which serves as the anode of the monopolar implant assembly 14(4), can be the same as that described above with respect to the pusher member 18(2).

Like the previous intermediate return electrode 186, the return electrode 386 may be coated with a layer of silver chloride to further reduce or prevent the generation of gaseous bubbles. To facilitate wicking of the saline or water into the detachment zone, a hydrophilic coating can be applied to one or both of the severable joint 20 and return electrode 386 in the same manner previously described above. In an alternative embodiment, only an edge of the intermediate return electrode 386 is exposed to the severable joint 20, thereby improving electrolyte perfusion and reducing the overall diameter of the implant assembly.

As illustrated, the return electrode 386 circumferentially extends around the severable joint 20. The insulative coating proximal and distal to the severable joint 20 provides a mechanical spacer that prevents contact between the severable joint 20 and the return electrode 386. Any portion of the proximal end of the stiffening member 380 can form the positive terminal 28 (shown in FIG. 2) that electrically communicates with the severable joint 20 via a forward electrical path that includes the coil wire of the stiffening member 380 and the coil 395.

The straight section 397 of the insulated coil 395 is threaded through the stretch resisting filament 70 and bent 180 degrees to form a link with the stretch resisting filament 70. The straight section 397 is then wound around, and mounted to, the return electrode 386 via suitable means, such as soldering or welding, or bonding using an electrically conductive adhesive, such as silver-filled epoxy. The newly formed windings of the insulated coil 395 fit between the open pitch windings of the primary coil 62 to minimize any increase in the outer diameter of the return electrode 386.

The pusher member 18(4) further comprises an electrically insulative sheath 396 disposed over the assembly, including the insulated coil 395, marker coil 392, and the stiffening member 380. The sheath 396 may be composed of a suitable polymeric material, such as PTFE or TFE, and have suitable dimensions (e.g., a wall thickness of 0.002 inches and an inner diameter of 0.006 inches). In the illustrated embodiment, the sheath 396 is heat shrunk over the assembly.

Although the implant assembly 14(4) has been described as a monopolar assembly, a bipolar implant assembly can be constructed by connecting the return electrode directly to ground return through a wire attached to the delivery catheter 12 (shown in FIGS. 1 and 2) or a wire extending through the pusher member 18(4). In this case, the primary coil 62 of the vaso-occlusive implant 22 can be electrically insulated from the return electrode 386.

Referring now to FIG. 10, another embodiment of a bipolar implant assembly 14(5) will now be described. The bipolar implant assembly 14(5) differs from the previously described bipolar implant assembly 14(1) in that it utilizes electrically conductive sheaths in the forward electrical path between the severable joint 20 and the positive electrode 28, and in the return electrical path between the return electrode and the negative terminal 30 (shown in FIG. 1).

The bipolar implant assembly 14(5) comprises the previously described vaso-occlusive implant 22 and a pusher member 18(5). The pusher member 18(5) comprises an elongated stiffening member 480 that includes a proximal stiffening member element 485 and a distal stiffening member element 487. The proximal stiffening member element 485 comprises an uninsulated core wire, and the distal stiffening member element 487 comprises an insulated core wire. The core wires of the stiffening member elements 485, 487 can be composed of any suitable electrically conductive and rigid material, such as stainless steel, and the coating can be composed of any suitable electrically insulative material, such as polyimide, PTFE, TFE, Parylene, PET, PBT, cyanoacrylate adhesives, or other suitable insulating layer.

The distal end of the proximal stiffening member element 485 includes a forked member 489 in which the proximal end of the distal stiffening member element 487 is mounted. The proximal end of the core wire in the distal stiffening member element 487 is left exposed, so that the proximal stiffening member element 485 is in electrical communication with the distal stiffening member element 487. An uninsulated wire is wrapped around the distal end of the proximal stiffening member element 485 to form a coil 491 that firmly secures the distal stiffening member element 487 within the forked member 489 of the proximal stiffening member element 485.

In the illustrated embodiment, the proximal stiffening member element 585 tapers from a large diameter section 481 to a small diameter section 483. The core wire of the proximal stiffening member element 485 can be ground to effect this taper. In the illustrated embodiment, the diameter of the core wire in the large diameter section 481 is 0.010 inches, and the diameter of the core wire in the small diameter section 483 is 0.0025 inches. The diameter of the core wire in the distal stiffening member element 487 is smaller than the core wire in the small diameter section 483 of the proximal stiffening member element 485; for example 0.0015 inches. The insulative coating on the core wire of the distal stiffening member element 487 may have a suitable thickness (e.g., 0.00035 inches).

Like the previously described stiffening member 80, the large diameter section 481 of the proximal stiffening member element 485 provides the pusher member 18(4) with lateral rigidity, as well as tensile strength, whereas the small diameter section 483 of the proximal stiffening member element 485 and even smaller diameter distal stiffening member element 487 provide the pusher member 18(5) with the desired lateral flexibility adjacent the vaso-occlusive implant 22 to minimize kickback during detachment of the vaso-occlusive implant 22. The electrolytic severable joint 20, which serves as the anode of the bipolar implant assembly 14(5), is formed on the distal stiffening member element 487 in the same manner as the severable joint 20 is formed on the core wire of the stiffening member 80 of the pusher member 18(1).

The pusher member 18(5) further comprises an electrically conductive coil 486 that serves as a return electrode (i.e., the cathode of the bipolar implant assembly 14(5)). The return electrode coil 486 may be formed by winding a wire having a suitable diameter (such as, e.g., 0.00175 inches) around a mandrel. The return electrode coil 486 has suitable dimensions; for example, an inner diameter of 0.006 inches (and thus an outer diameter of 0.0095 inches) and a length of 0.75 mm. The return electrode coil 486 may be composed of a suitable electrically conductive material, such as silver or copper. In the illustrated embodiment, the return electrode coil 486 has an open pitch (e.g., 20%) to increase its lateral flexibility. The return electrode coil 486 circumferentially extends around the severable joint 20 and is spatially isolated from the severable joint 20 via a spacer element 490 mounted to the distal stiffening member element 487 at a location proximal to the severable joint 20 using a suitable adhesive. The spacer element 490 may take the same form and be constructed of the same materials as the spacer element 90 described above. Like the previous return electrode coil 86, the return electrode coil 486 serves as a compression element and may be coated with a layer of silver chloride to further prevent or reduce the generation of gaseous bubbles.

The pusher member 18(5) comprises an electrically conductive sheath 493 bonded around the smaller diameter section 483 of the proximal stiffening member element 485 using suitable means, such as silver-filled epoxy or shrink tubing. In the illustrated embodiment, the electrically conductive sheath 493 extends from the proximal end of the small diameter section 483 of the proximal stiffening member element 485 to the distal end of the small diameter section 483 of the proximal stiffening member element 485 just proximal to the securing coil 491. The pusher member 18(5) further comprises an electrically insulative sheath 497 disposed over the proximal stiffening member element 485, electrically conductive sheath 493, and securing coil 491. The pusher member 18(5) further comprises another electrically conductive sheath 498 suitably bonded around the electrically insulative sheath 497 coincident with the large diameter section 481 of the proximal stiffening member element 485, using suitable means, such epoxy. The pusher member 18(5) further comprises an electrically insulative sheath 496 disposed over the assembly, including the return electrode coil 486, marker coil 492, and flex coil 495.

The electrically conductive sheaths 493, 498 may take the form of, e.g., a mesh, braid, or coil. In the embodiment illustrated in FIG. 10, the electrically conductive sheaths 493, 498 take the form of mesh. While the core wire of the stiffening member 480 is preferably composed of a material that has a greater durometer than the material from which the electrically conductive sheaths 493, 498 are composed; for example, stainless steel, the electrically conductive sheaths 493, 498 are preferably composed of a material that is more electrically conductive than the material from which core wire of the stiffening member 480 is composed; for example, silver or copper. The electrically insulative sheaths 496, 497 may be composed of a suitable polymeric material, such as PTFE or TFE, and have suitable dimensions (e.g., a wall thickness of 0.002 inches and an inner diameter of 0.006 inches).

Significantly, the sheath 496 circumferentially surrounds both the severable joint 20 and the return electrode coil 486. Thus, like the previously described sheath 96 of the bipolar pusher member 18(1), the sheath 496 increases the compressive strength of the pusher member 18(5), and reduces diffusion and convection of an ideal electrolytic environment away from the detachment region when the implant assembly 14(5) is exposed to the bodily fluids. As previously described, such ideal electrolytic environment can be created by introducing the ideal electrolyte into the detachment region or introducing water into the detachment region previously coated with salt. To facilitate wicking of the saline or water into the detachment zone, a hydrophilic coating can be applied to one or both of the severable joint 20 and return electrode coil 486 in the same manner previously described above.

The pusher member 18(5) further comprises a radiopaque marker, and in particular a platinum marker coil 492, circumferentially extending around the small diameter section 483 of the proximal stiffening member element 485. The marker coil 492 may be formed and constructed of the same material as the marker coil 92 described above. The pusher member 18(5) further comprises a flex coil 495 circumferentially extending around the small diameter section 483 of the proximal stiffening member element 485 just proximal to the marker coil 492. The flex coil 495 is composed of an electrically conductive material, such as stainless steel. In the illustrated embodiment, the flex coil 495 has a closed pitch. The marker coil 492 and flex coil 495 preferably have the same diameter as the return coil 486.

The pusher member 18(5) further comprises an electrical conductor 494 connected between the return electrode coil 486 and the other electrically conductive sheath 498 via suitable means, such as soldering or welding, or bonding using an electrically conductive adhesive, such as silver-filled epoxy. The electrical conductor 492 may be a copper or silver wire. In the illustrated embodiment, the electrical conductor 494 is disposed on the outside of the electrically insulative sheath 497 to ensure electrically isolation of the electrical conductor 492 from the stiffening member 480, and thus, electrical isolation between the return electrode coil 486 and the severable joint 20. The electrical conductor 492 has suitable dimensions, such as, e.g., a wire diameter of 0.0015 inches and a total diameter (including insulation) of 0.002 inches.

The pusher member 18(5) further comprises an electrically insulative sheath 496 disposed over the assembly, including the return electrode coil 486, marker coil 492, and flex coil 495. The sheath 496 may be composed of a suitable polymeric material, such as PTFE, and have suitable dimensions (e.g., a wall thickness of 0.002 inches and an inner diameter of 0.006 inches). In the illustrated embodiment, the sheath 496 is heat shrunk over the assembly.

A portion of the core wire in the proximal stiffening member element 485, and in the illustrated embodiment the proximal tip of the proximal stiffening member element 485, is left exposed to form the positive terminal 28 (shown in FIG. 1) that electrically communicates with the severable joint 20 via a forward electrical path that includes the stiffening member 480 and the electrically conductive sheath 493. Advantageously, the stiffening member 480 provides the necessary pushability for the implant assembly 14(5), while the high electrically conductive sheath 493 significantly decreases the electrical conductance along the portion of the forward electrical path that is coincident with the small diameter section 483 of the proximal stiffening member element 485 where the electrical conductance would otherwise decrease relative to the large diameter section 481 of the proximal stiffening member element 485.

The pusher member 18(5) further comprises an electrically conductive terminal ribbon 499, which serves as the negative terminal 30 (shown in FIG. 1), mounted around the other electrically conductive sheath 498 at a location at the proximal end of the proximal stiffening member element 485. The terminal ribbon 499 may be composed of a material, such as silver or copper, and is electrically coupled to the return electrode coil 486. Thus, the terminal ribbon 499 electrically communicates with the return electrode coil 486 via a return electrical path that includes the other electrically conductive sheath 498 and electrical conductor 494. Advantageously, the high electrically conductive sheath 498 significantly decreases the electrical conductance along the return electrical path compared to a case where the electrical conductor 494 extends the full length between the return electrode coil 486 and the terminal ribbon 499.

Referring now to FIG. 11, still another embodiment of a bipolar implant assembly 14(6) will now be described. The bipolar implant assembly 14(6) differs from the previously described bipolar implant assembly 14(5) in that it utilizes only one electrically conductive sheath in the return electrical path between the return electrode and the negative terminal 30 (shown in FIG. 1). The bipolar implant assembly 14(5) comprises the previously described vaso-occlusive implant 22 and a pusher member 18(6).

The pusher member 18(6) comprises an elongated stiffening member 580 that is similar to the previously described stiffening member 480, with the exception that substantially the entire length of the stiffening member 580 is insulated. Thus, the stiffening member 580 includes a tapered proximal stiffening member element 585 having a large diameter section 581 and a small diameter section 583, and a distal stiffening member element 587. The distal end of the proximal stiffening member element 585 has forked member 589 in which the proximal end of the distal core wire element 587 is mounted via a securing coil 591. The construction and dimensions of the proximal stiffening member element 585, distal stiffening member element 587, and securing coil 591 may be the same as the proximal stiffening member element 485, distal stiffening member element 487, and securing coil 491 described above, with the exception that both stiffening member elements 585, 587 comprise core wires coated with an electrically insulative material.

Like the previously described stiffening member 80, the large diameter section 581 of the proximal stiffening member element 585 provides the pusher member 18(6) with lateral rigidity, as well as tensile strength, whereas the small diameter section 583 of the proximal stiffening member element 585 and even smaller diameter distal stiffening member element 587 provide the pusher member 18(6) with the desired lateral flexibility adjacent the vaso-occlusive implant 22 to minimize kickback during detachment of the vaso-occlusive implant 22. The electrolytic severable joint 20, which serves as the anode of the bipolar implant assembly 14(6), is formed on the distal stiffening member element 587 in the same manner as the severable joint 20 is formed on the stiffening member 80 of the pusher member 18(1).

The pusher member 18(6) comprises an electrically conductive sheath 598 suitably bonded around the proximal stiffening member element 585 using suitable means, such epoxy. The electrically conductive sheath 598 may take the form of, e.g., a mesh, braid, or coil. In the illustrated embodiment, the electrically conductive sheath 598 is a coil. The electrically conductive sheath 598 is composed of a material that is more electrically conductive than the material from which the stiffening member 580 is composed; for example, silver or copper.

The pusher member 18(6) further comprises an electrically conductive coil 586 that serves as a return electrode (i.e., the cathode of the bipolar implant assembly 14(6)), a radiopaque marker, and in particular a platinum marker coil 592, and a flex coil 595 that circumferentially extend around the stiffening member 590 in the same manner as the respective return electrode coil 486, marker coil 492, and flex coil 495 described above. That is, the proximal end of the return electrode coil 586 is bonded around the securing coil 591, and the marker coil 592 and flex coil 595 are bonded around the electrically conductive sheath 598 along the small diameter section 583 of the proximal stiffening member element 585. The return electrode coil 586 is spatially isolated from the severable joint 20 via a spacer element 590 mounted to the distal stiffening member element 587 at a location proximal to the severable joint 20 using a suitable adhesive.

The return electrode coil 586, marker coil 592, flex coil 595, and spacer element 590 may take the same form and be constructed of the same materials as the respective return electrode coil 486, marker coil 492, flex coil 495, and spacer element 490 described above. Like the previous return electrode coil 86, the return electrode coil 586 serves as a compression element and may be coated with a layer of silver chloride to further prevent or reduce the generation of gaseous bubbles.

The pusher member 18(6) further comprises an electrically insulative sheath 596 disposed over the assembly, including the return electrode coil 586, marker coil 592, and flex coil 595. The sheath 596 may be composed of the same material and have the same dimensions as the sheath 496 described above. Significantly, the sheath 596 circumferentially surrounds both the severable joint 20 and the return electrode coil 586. Thus, like the previously described sheath 96 of the bipolar pusher member 18(1), the sheath 596 increases the compressive strength of the pusher member 18(6), and reduces diffusion and convection of an ideal electrolytic environment away from the detachment region when the implant assembly 14(6) is exposed to the bodily fluids. As previously described, such ideal electrolytic environment can be created by introducing the ideal electrolyte into the detachment region or introducing water into the detachment region previously coated with salt. To facilitate wicking of the saline or water into the detachment zone, a hydrophilic coating can be applied to one or both of the severable joint 20 and return electrode coil 586 in the same manner previously described above.

The core wire in a portion of the proximal stiffening member element 585, and in the illustrated embodiment the proximal tip of the core wire, is left exposed to form the positive terminal 28 (shown in FIG. 1) that electrically communicates with the severable joint 20 via a forward electrical path formed only by the stiffening member 580. Any portion of the electrically conductive sheath 598 may serve as the negative terminal 30 (shown in FIG. 1). Thus, the entire electrically conductive sheath 598 forms the forward electrical path to the return electrode coil 586. Advantageously, the high electrically conductive sheath 586 significantly decreases the electrical conductance along the electrical path to the return electrode coil 586 compared to a standard wire that may otherwise extend between the return electrode coil 586 and the negative terminal 30.

Referring now to FIG. 12, yet another embodiment of a bipolar implant assembly 14(7) will now be described. The bipolar implant assembly 14(7) differs from the previously described bipolar implant assembly 14(5) in that it utilizes coils, instead of mesh, for the electrically conductive sheaths. To this end, the bipolar implant assembly 14(7) comprises the previously described vaso-occlusive implant 22 and a pusher member 18(7).

The pusher member 18(7) comprises an elongated stiffening member 680 that is similar to the previously described stiffening member 480. In particular, the stiffening member 680 includes a tapered proximal stiffening member element 685 having a large diameter section 681 and a small diameter section 683, and a distal stiffening member element 687. The distal end of the proximal stiffening member element 685 has forked member 689 in which the proximal end of the distal core wire element 687 is mounted via a securing coil 691. The construction and dimensions of the proximal stiffening member element 685, distal stiffening member element 687, and securing coil 691 may be the same as the proximal stiffening member element 485, distal stiffening member element 487, and securing coil 491 described above.

Like the previously described stiffening member 80, the large diameter section 681 of the proximal stiffening member element 585 provides the pusher member 18(7) with lateral rigidity, as well as tensile strength, whereas the small diameter section 683 of the proximal stiffening member element 685 and even smaller diameter distal stiffening member element 687 provide the pusher member 18(7) with the desired lateral flexibility adjacent the vaso-occlusive implant 22 to minimize kickback during detachment of the vaso-occlusive implant 22. The electrolytic severable joint 20, which serves as the anode of the bipolar implant assembly 14(7), is formed on the distal stiffening member element 687 in the same manner as the severable joint 20 is formed on the stiffening member 80 of the pusher member 18(1).

The pusher member 18(7) comprises an electrically conductive sheath 693 bonded around the smaller diameter section 683 of the proximal stiffening member element 685 using suitable means, such as silver-filled epoxy or shrink tubing. In the illustrated embodiment, the electrically conductive sheath 693 extends from the proximal end of the small diameter section 683 of the proximal stiffening member element 685 to the distal end of the small diameter section 683 of the proximal stiffening member element 685 just proximal to the securing coil 691. The pusher member 18(7) further comprises an electrically insulative sheath 697 disposed over the proximal stiffening member element 685, electrically conductive sheath 693, and securing coil 691. The pusher member 18(7) further comprises another electrically conductive sheath 698 suitably bonded around the electrically insulative sheath 697 coincident with the large diameter section 681 of the proximal stiffening member element 685, as well as a large portion of the small diameter section 683 of the proximal stiffening member element 685, using suitable means, such epoxy. The pusher member 18(7) further comprises an electrically insulative sheath 696 disposed over the assembly, including the return electrode coil 686, marker coil 692, and portion of the electrically conductive sheath 698.

The electrically conductive sheaths 693, 698 may take the form of, e.g., a mesh, braid, or coil. In the embodiment illustrated in FIG. 12, the electrically conductive sheaths 693, 698 take the form of coils. The electrically conductive sheaths 693, 698 are preferably composed of a material that is more electrically conductive than the material from which core wire of the stiffening member 680 is composed; for example, silver or copper. The electrically insulative sheaths 696, 697 may be composed of a suitable polymeric material, such as PTFE or TFE, and have suitable dimensions (e.g., a wall thickness of 0.002 inches and an inner diameter of 0.006 inches).

The pusher member 18(6) further comprises an electrically conductive coil 686 that serves as a return electrode (i.e., the cathode of the bipolar implant assembly 14(6)), and a radiopaque marker, and in particular a platinum marker coil 692 that circumferentially extend around the stiffening member 690 in the same manner as the respective return electrode coil 486 and marker coil 492 described above. That is, the proximal end of the return electrode coil 686 is bonded around the securing coil 691, and the marker coil 692 is bonded around the electrically conductive sheath 698 along the small diameter section 683 of the proximal stiffening member element 685. Notably, the electrically conductive sheath 698 serves as a flex coil, and thus, a separate flex coil is not needed in this embodiment.

The return electrode coil 686 is spatially isolated from the severable joint 20 via a spacer element 690 mounted to the distal stiffening member element 587 at a location proximal to the severable joint 20 using a suitable adhesive. The return electrode coil 686, marker coil 692, and spacer element 690 may take the same form and be constructed of the same materials as the respective return electrode coil 486, marker coil 492, and spacer element 490 described above. Like the previous return electrode coil 86, the return electrode coil 686 serves as a compression element and may be coated with a layer of silver chloride to further prevent or reduce the generation of gaseous bubbles.

Significantly, the sheath 696 circumferentially surrounds both the severable joint 20 and the return electrode coil 686. Thus, like the previously described sheath 96 of the bipolar pusher member 18(1), the sheath 696 increases the compressive strength of the pusher member 18(7), and reduces diffusion and convection of an ideal electrolytic environment away from the detachment region when the implant assembly 14(7) is exposed to the bodily fluids. As previously described, such ideal electrolytic environment can be created by introducing the ideal electrolyte into the detachment region or introducing water into the detachment region previously coated with salt. To facilitate wicking of the saline or water into the detachment zone, a hydrophilic coating can be applied to one or both of the severable joint 20 and return electrode coil 686 in the same manner previously described above.

A core wire at a portion of the proximal stiffening member 685, and in the illustrated embodiment the proximal tip of the core wire, is left exposed to form the positive terminal 28 (shown in FIG. 1) that electrically communicates with the severable joint 20 via a forward electrical path formed only by the stiffening member 680. Any portion of the electrically conductive sheath 698 may serve as the negative terminal 30 (shown in FIG. 1). Thus, like the previously described electrically conductive sheaths 593, 598, the electrically conductive sheaths 693, 698 increase the conductance of the forward electrical path to the severable joint 20 and the return electrode path from the return electrode coil 686.

Having described the arrangement and function of the medical system 10, a method of its use in occluding an aneurysm 702 within a blood vessel 700 will now be described with reference to FIGS. 13A-13C. The vaso-occlusive device 23 (shown in FIG. 8) can similarly be delivered to the aneurysm 702 in the following manner, but for the purposes of brevity, only delivery of the vaso-occlusive device 23 will be described in detail.

Figure 13A:
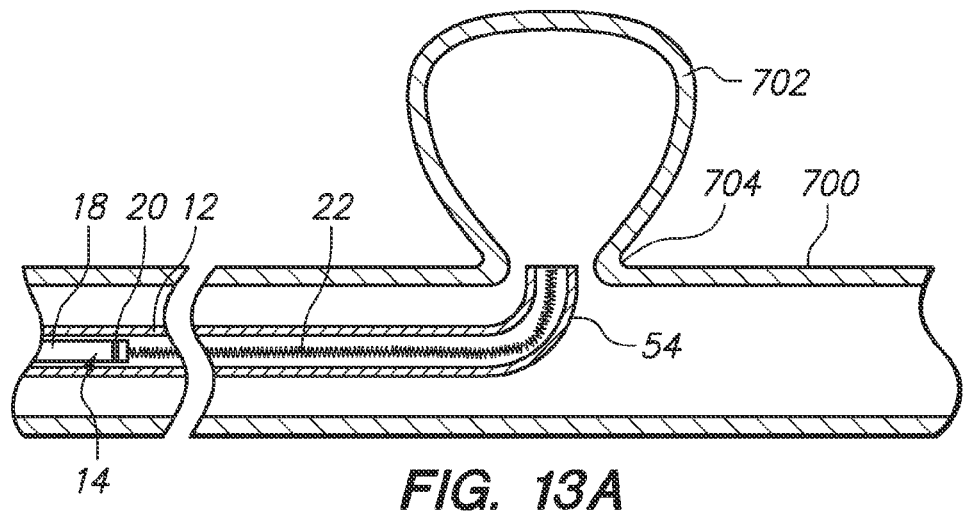
FIGS. 13A-13C are cross-sectional views illustrating a method of delivering a vaso-occlusive device within an aneurysm of the patient utilizing the medical systems of FIG. 1 or FIG. 2.

Turning specifically to FIG. 13A, the delivery catheter 12 is steered just within a neck 704 of the aneurysm 702. At this point, the vaso-occlusive device 22 is in its undeployed shape, and is coupled to the pusher member 18 via the electrolytically severable joint 20. The implant assembly 14 is situated within the lumen of the delivery catheter 12, such that the vaso-occlusive device 22 resides within the distal end 54 of the delivery catheter 12.

Figure 13B:
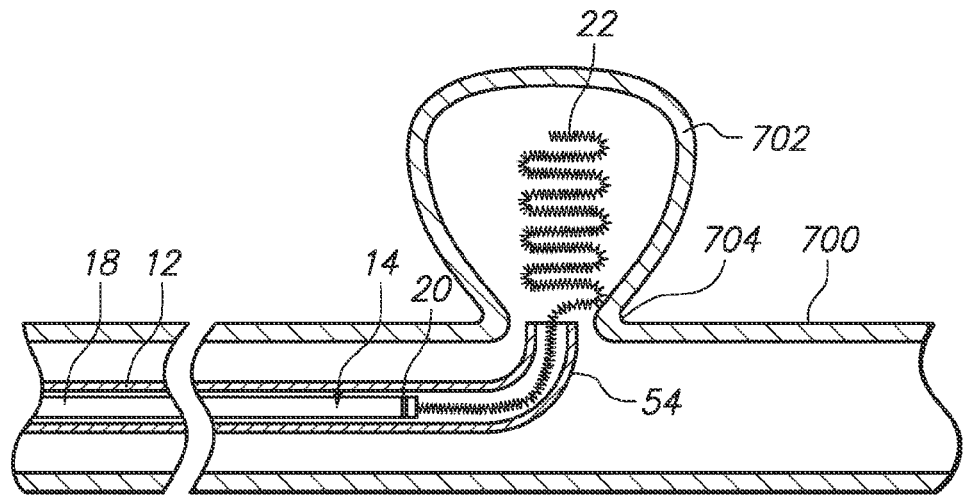

Turning to FIG. 13B, the pusher member 18 is then pushed in the distal direction relative to the delivery catheter 12, causing the vaso-occlusive device 22 to extend out of the distal end 54 of the delivery catheter 12, through the neck 704, and into the aneurysm 702. As the vaso-occlusive device 22 is pushed out of the delivery catheter 12, the portion of the vaso-occlusive device 22 that is free from the constraints of the delivery catheter 12 can assume its deployed shape.

Figure 13C:
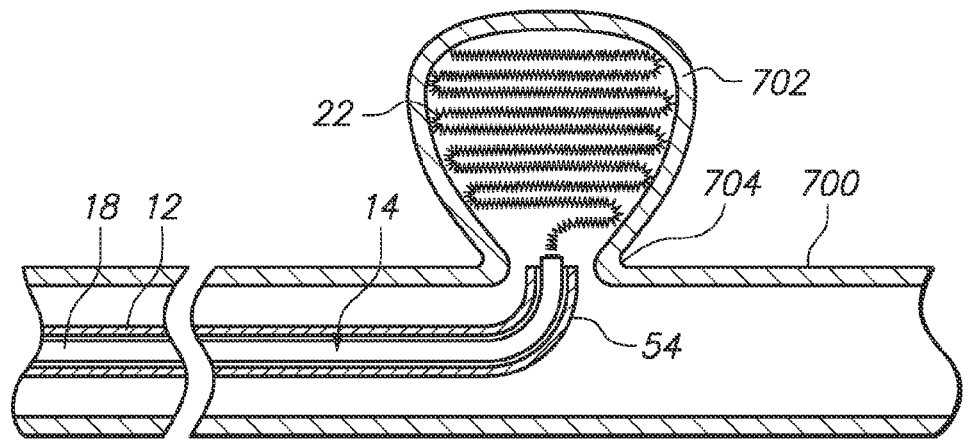

Turning to FIG. 13C, the pusher member 18 continues to be pushed in the distal direction relative to the delivery catheter 12 until the entire vaso-occlusive device 22 is deployed within the aneurysm 702. The vaso-occlusive device 22 is then detached from the pusher member 18 by conveying an electrical current through the pusher member 18 to electrolytically dissolve the severable joint 20.

In a bipolar arrangement (shown in FIG. 1), detachment of the vaso-occlusive device 22 can be accomplished by conveying electrical current from the positive terminal 34 of the power supply 16 to the positive terminal 28 of the pusher member 18, and along the forward electrical path within the pusher member 18 to the severable joint 20, and conveying electrical current from the return electrode on the pusher member 18, back along the return electrical path within the pusher member 18, and then from the negative terminal 30 of the pusher member 18 to the negative terminal 36 of the power supply 16. Additional vaso-occlusive devices 22 can be deployed within the aneurysm 702 as needed by removing the pusher member 18 from the delivery catheter 12, inserting another implant assembly 14 within the lumen of the delivery catheter 12, and repeating the steps illustrated in FIGS. 13B and 13C.

In a monopolar arrangement (shown in FIG. 2), detachment of the vaso-occlusive device 22 can be accomplished by conveying electrical current from the positive terminal 34 of the power supply 16 to the positive terminal 28 of the pusher member 18, and along the forward electrical path within the pusher member 18 to the severable joint 20, and conveying electrical current from the return electrode (if available) on the pusher member 18, back along the return electrical path within the patient's body, and then from the ground electrode 32 (shown in FIG. 2) to the negative terminal 36 of the power supply 16.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implant assembly, comprising: an elongated pusher member, comprising
   an electrically insulative sheath having a sheath lumen,
   an electrically insulated core wire extending through the sheath lumen, the core wire having a non-insulated electrolytically severable portion located within a distal portion of the sheath lumen, and
   a return electrode defining a return electrode lumen and having a terminal portion disposed within the distal portion of the sheath lumen, wherein the sheath, the core wire, and the return electrode are fixably attached to one another, wherein the return electrode extends circumferentially around the severable portion; and
   an implantable device attached to the core wire distal of the severable portion,
   wherein the sheath has an open distal end in communication with the sheath lumen such that, when the distal end of the assembly is implanted in a blood vessel, blood enters the sheath lumen through the open distal end and forms an electrical pathway between the electrolytically severable portion and the return electrode.

2. The implant assembly of claim 1, wherein the core wire extends through the return electrode lumen.

3. The implant assembly of claim 2, where the severable portion is disposed in the return electrode lumen.

4. The implant assembly of claim 1, wherein the implantable device comprises a vaso-occlusive device.

5. The implant assembly of claim 1, wherein at least one of the severable portion and the return electrode has a hydrophilic coating.

6. The implant assembly of claim 1, wherein the return electrode is a coil having a coil lumen, and wherein the core wire passes through the coil lumen.

7. The implant assembly of claim 6, where the severable portion is disposed in the coil lumen.

8. The implant assembly of claim 1, further comprising an electrically insulative spacer fixably attached to the core wire, the spacer preventing contact between the core wire and the return electrode.

9. The implant assembly of claim 1, wherein the insulative sheath is composed of a polymeric material.

* * * * *